United States Patent
Kemmoku et al.

(10) Patent No.: US 10,351,512 B2
(45) Date of Patent: Jul. 16, 2019

(54) METHOD OF PRODUCING ORGANIC COMPOUND

(71) Applicant: FUJIFILM Wako Pure Chemical Corporation, Osaka-shi (JP)

(72) Inventors: Akira Kemmoku, Osaka (JP); Yayoi Haga, Osaka (JP); Fumio Kawamoto, Osaka (JP)

(73) Assignee: FUJIFILM Wako Pure Chemical Corporation, Osaka-shi (JP)

( * ) Notice: Subject to any disclaimer, the term of this patent is extended or adjusted under 35 U.S.C. 154(b) by 0 days.

(21) Appl. No.: 15/751,217

(22) PCT Filed: Sep. 28, 2016

(86) PCT No.: PCT/JP2016/078623
§ 371 (c)(1),
(2) Date: Feb. 8, 2018

(87) PCT Pub. No.: WO2017/057460
PCT Pub. Date: Apr. 6, 2017

(65) Prior Publication Data
US 2018/0244604 A1    Aug. 30, 2018

(30) Foreign Application Priority Data
Sep. 30, 2015   (JP) .................................. 2015-195375

(51) Int. Cl.
| | | |
|---|---|---|
| C07C 45/29 | (2006.01) |
| C07C 315/00 | (2006.01) |
| C07C 317/04 | (2006.01) |
| C07C 225/22 | (2006.01) |
| C07B 33/00 | (2006.01) |
| C07B 63/00 | (2006.01) |
| C07H 17/08 | (2006.01) |
| C07C 221/00 | (2006.01) |
| C07C 223/06 | (2006.01) |
| C07J 1/00 | (2006.01) |
| C07C 47/02 | (2006.01) |
| C07C 47/228 | (2006.01) |
| C07C 49/04 | (2006.01) |
| C07C 49/403 | (2006.01) |
| C07C 49/786 | (2006.01) |
| C07C 49/807 | (2006.01) |
| C07D 213/50 | (2006.01) |
| C07D 307/46 | (2006.01) |
| C07C 47/232 | (2006.01) |
| C07C 49/303 | (2006.01) |
| C07C 49/76 | (2006.01) |
| C07C 49/78 | (2006.01) |
| C07D 307/48 | (2006.01) |
| C07D 493/04 | (2006.01) |
| C07C 315/02 | (2006.01) |

(52) U.S. Cl.
CPC ............ *C07C 225/22* (2013.01); *C07B 33/00* (2013.01); *C07B 63/00* (2013.01); *C07C 45/29* (2013.01); *C07C 47/02* (2013.01); *C07C 47/228* (2013.01); *C07C 47/232* (2013.01); *C07C 49/04* (2013.01); *C07C 49/303* (2013.01); *C07C 49/403* (2013.01); *C07C 49/76* (2013.01); *C07C 49/78* (2013.01); *C07C 49/786* (2013.01); *C07C 49/807* (2013.01); *C07C 221/00* (2013.01); *C07C 223/06* (2013.01); *C07D 213/50* (2013.01); *C07D 307/46* (2013.01); *C07D 307/48* (2013.01); *C07D 493/04* (2013.01); *C07H 17/08* (2013.01); *C07J 1/00* (2013.01); *C07C 315/02* (2013.01); *C07C 317/04* (2013.01); *C07C 2601/14* (2017.05)

(58) Field of Classification Search
CPC ...... C07C 45/29; C07C 315/07; C07C 317/04
See application file for complete search history.

(56) References Cited

U.S. PATENT DOCUMENTS

| | | | | |
|---|---|---|---|---|
| 6,267,941 | B1 * | 7/2001 | Sata ........................ | A61L 9/00 423/213.2 |
| 2006/0036096 | A1 | 2/2006 | Nagashima et al. | |
| 2008/0146804 | A1 | 6/2008 | Stumpf | |

FOREIGN PATENT DOCUMENTS

| | | |
|---|---|---|
| JP | 2003-171332 A | 6/2003 |
| JP | 2003-313151 A | 11/2003 |
| JP | 2006-246855 A | 9/2006 |
| JP | 2007-520563 A | 7/2007 |
| JP | 2008-214257 A | 9/2008 |
| WO | 2004/041787 A1 | 5/2004 |

OTHER PUBLICATIONS

International Search Report dated Dec. 27, 2016 in PCT/JP2016/078623 filed Sep. 28, 2016.
Kanji Omura et al., "Dimethyl Sulfoxide-Trifluoroacetic Anhydride: a New Reagent for Oxidation of Alcohols to Carbonyls", Journal of Organic Chemistry, 1976, vol. 41, No. 6, pp. 957-962.

(Continued)

*Primary Examiner* — Sikarl A Witherspoon
(74) *Attorney, Agent, or Firm* — Oblon, McClelland, Maier & Neustadt, L.L.P.

(57) ABSTRACT

A method of producing an organic compound, which contains a step of performing a deodorization step using a flow reaction in a flow passage to remove, from a reaction liquid, a malodorous material generated or remaining in a reaction step, wherein the organic compound is an industrially useful compound.

21 Claims, 2 Drawing Sheets

(56) References Cited

OTHER PUBLICATIONS

E. J. Corey et al., "A New and Highly Effective Method for the Oxidation of Primary and Secondary Alcohols to Carbonyl Compounds", Journal of the American Chemical Society, Oct. 18, 1972, vol. 94, No. 21, pp. 7586-7587.
Extended European Search Report dated Mar. 21. 2019 in corresponding EP Application No. 16851631.8, filed Sep. 28, 2016, 6 pages.
Anonymous: "Swern Oxidation; Chem-Station Int. Ed.", Mar. 12, 2014; XP55567681, Retrieved from the Internet: URL:https://en.chem-station.com/reactions-2/2014103/swern-oxidation.html [retrieved on Mar. 12, 2019]. *Experimental Tips*, 10 pgs.

* cited by examiner

Fig. 1

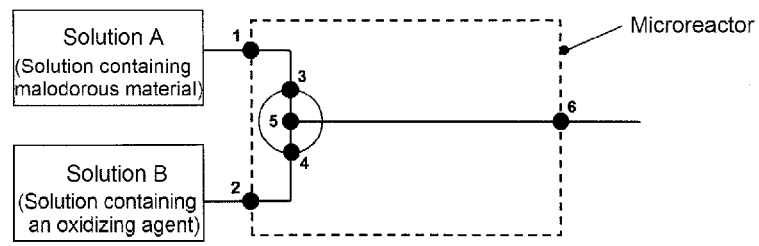

Points 1, 2 : Port for supplying a raw material to the microreactor
Points 3, 4 : Port for supplying a raw material to the micromixer
Point 5 : Start point of mixing of the solutions A and B
Point 6 : Exit of the microreactor
Section 1~3 : Section for controlling the temperature of solution A
Section 2~4 : Section for controlling the temperature of solution B
Section 5~6 : Section for the reaction between solutions A and B

Fig. 2

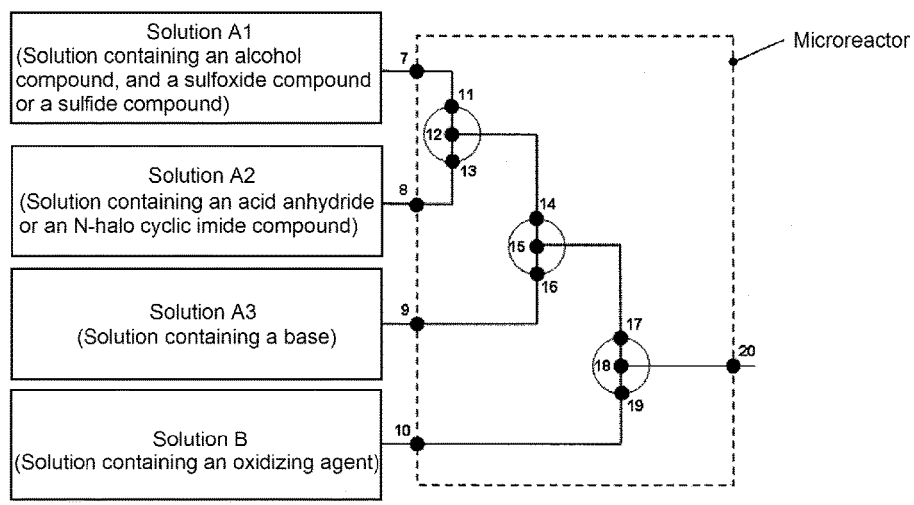

Points 7, 8, 9, 10 : Port for supplying a raw material to the microreactor
Points 11, 13, 14, 16, 17, 19 : Port for supplying a raw material to the micromixer
Point 12 : Mixing start point in a first step (a reaction between solutions A1 and A2)
Point 15 : Mixing start point in a second step (a reaction with solution A3)
Point 18 : Mixing start point in a third step (a reaction with solution B)
Point 20 : Exit of the microreactor
Section 7~11 : Section for controlling the temperature of solution A1
Section 8~13 : Section for controlling the temperature of solution A2
Section 9~16 : Section for controlling the temperature of solution A3
Section 10~19 : Section for controlling the temperature of solution B
Section 12~14 : Section for the reaction in the first step
Section 15~17 : Section for the reaction in the second step
Section 18~20 : Section for the reaction in the third step

METHOD OF PRODUCING ORGANIC COMPOUND

TECHNICAL FIELD

The present invention relates to a method of producing an industrially useful organic compound.

More specifically, the present invention relates to a method of producing an industrially useful organic compound, the method containing a deodorization step including performing a flow reaction in a flow passage to remove from a reaction liquid a malodorous material generated in a reaction step.

BACKGROUND ART

In production of organic compounds, some malodorous materials may be generated by reaction or remain after reaction, which can not only result in working environment pollution and working efficiency reduction but also place a burden on the environment and human health.

Deodorization techniques used conventionally include, for example, cleaning methods, adsorption methods, combustion methods, biological deodorization methods, ozone deodorization methods, photo-catalyst deodorization methods, plasma deodorization methods, refresher or deodorizer methods, and dilution or diffusion methods. Generally, in each of these deodorization methods, the generated malodorous material is once directed to outside the reaction system and then treated outside the reaction system using an appropriate deodorization technique.

In addition, cleaning, adsorption, and combustion methods are generally used in combination because malodorous materials generated by chemical reaction contain an organic solvent used in the reaction.

However, the combination of such methods described above has problems such as manufacturing equipment enlargement, high costs, and high environmental burden. In addition, the process of directing malodorous materials to outside the reaction system requires a measure to prevent the diffusion of the malodor from the manufacturing equipment, such as a closed system for the entire equipment, which increases the equipment cost.

There has been proposed a method of removing malodorous materials from foods and beverages using a hollow fiber membrane (see Patent Literature 1), in which the malodorous materials are not those generated by chemical reaction or remaining after chemical reaction. Unfortunately, this method is not practical for removing malodorous materials generated by chemical reaction or remaining after chemical reaction, owing to problems with the solvent resistance of the membrane to organic solvents for use in reactions or in view of the cost required to introduce treatment equipment.

Oxidation reactions for synthesizing aldehyde or ketone compounds by oxidation of alcohol compounds are typical examples of chemical reactions in which the reaction step can generate an offensive odor material being a malodorous material or the odor material can remain after the reaction step. Such oxidation reactions are very important for organic synthesis. Swern oxidation is a typical oxidation reaction. Swern oxidation is widely used as laboratory-scale oxidation because it does not generate any heavy metal-containing waste, has a wide range of applicable compounds, and does not bring about excessive oxidation. However, Swern oxidation has the problem of by-production of dimethyl sulfide, which is toxic and strongly malodorous, after the oxidation reaction, because it uses oxalyl chloride or trifluoroacetic anhydride, and dimethyl sulfoxide (DMSO) as activators (see Non-Patent Literature 1).

Corey-Kim oxidation is a useful method that uses reaction conditions milder than those for Swern oxidation and can selectively produce an aldehyde or ketone compound from an alcohol compound even when the alcohol compound has an oxidation-sensitive substituent, such as an amino group, in the molecule (Non-Patent Literature 2). However, measures against the offensive odor of dimethyl sulfide (DMS) are a problem with Corey-Kim oxidation, which uses dimethyl sulfide and N-chlorosuccinimide as activators. There has been also developed a modified method using dodecyl methyl sulfide, which is less malodorous (see Patent Literature 2). However, such a method has problems such as high cost and complicated treatment of the sulfide compound after the reaction.

Therefore, Swern oxidation and Corey-Kim oxidation have not been popular for industrial use, though they are very useful for the synthesis of aldehyde or ketone compounds by oxidation reaction of alcohol compounds.

CITATION LIST

Patent Literatures

Patent Literature 1: JP-A-2006-246855 ("JP-A" means unexamined published Japanese patent application)
Patent Literature 2: JP-A-2003-313151

Non-Patent Literatures

Non-Patent Literature 1: J. Org. Chem., 1976, 41, 957-962
Non-Patent Literature 2: J. Am. Chem. Soc., 1972, 94, 7586-7587

SUMMARY OF INVENTION

Technical Problem

Under these circumstances described above, a need is felt for the development of a method capable of producing an aldehyde or ketone compound by oxidation reaction of an alcohol compound with little concern about irritating or unpleasant odor, with simple aftertreatment, and with low cost burden.

In addition, it is necessary to develop a deodorization method capable of easily and inexpensively removing malodorous materials not only in Swern oxidation or Corey-Kim oxidation but also in production of a variety of industrially useful organic compounds.

Therefore, the present invention contemplates providing a production method of industrially useful organic compounds wherein malodorous materials generated in a reaction step can be easily and inexpensively removed, with a lower environmental burden.

Solution to Problem

As a result of intensive studies, the inventors have found that the problems described above can be resolved by the following means.
(1) A method of producing an organic compound, which contains a step of performing a deodorization step using a flow reaction in a flow passage to remove from a reaction liquid a malodorous material generated or remaining in a reaction step, wherein the organic compound is an industrially useful compound.

(2) The production method described in the above item (1), wherein the reaction step is an oxidation reaction using a sulfur atom-containing organic compound.

(3) The production method described in the above item (1) or (2), wherein, in the reaction step, an alcohol compound having 2 to 50 carbon atoms is oxidized to produce an aldehyde or ketone compound having 2 to 50 carbon atoms.

(4) The production method described in the above item (2) or (3), wherein the oxidation reaction using a sulfur-atom-containing organic compound is an oxidation reaction using a dialkyl sulfoxide compound having 2 to 8 carbon atoms, and an acid anhydride having 4 to 10 carbon atoms or an acid halide having 2 to 7 carbon atoms.

(5) The production method described in any one of the above items (1) to (4), wherein the malodorous material is a dialkyl sulfide having 2 to 8 carbon atoms.

(6) The production method described in any one of the above items (1) to (5), wherein the deodorization step is an oxidation reaction of the malodorous material.

(7) The production method described in any one of the above items (1) to (6), wherein the deodorization step is an oxidation reaction in which the malodorous material is oxidized by using an oxidizing agent selected from the group consisting of hypochlorous acid or a salt thereof, a halogenating agent, and peracetic acid.

(8) The production method described in the above item (7), wherein the amount of the oxidizing agent to be used is 0.5 to 5.0 molar equivalents, based on the amount of the acid anhydride or the acid halide to be used in the reaction step.

(9) The production method described in any one of the above items (1) to (8), wherein the reaction temperature in the deodorization step is from −20° C. to 60° C.

(10) The production method described in any one of the above items (1) to (9), wherein the time for which the deodorization step is retained in the flow passage (reaction time) is from 0.01 to 120 seconds.

(11) The production method described in any one of the above items (3) to (10), wherein the alcohol compound is a compound represented by Formula (A), and the organic compound is a compound represented by Formula (B):

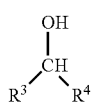

Formula (A)

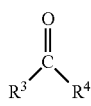

Formula (B)

wherein $R^3$ represents a hydrogen atom, an alkyl group, a cycloalkyl group, an alkenyl group, a cycloalkenyl group, an aryl group, or a heterocyclic group; $R^4$ represents an alkyl group, a cycloalkyl group, an alkenyl group, a cycloalkenyl group, an aryl group, or a heterocyclic group; and $R^3$ and $R^4$ may combine together to form a ring.

(12) The production method described in any one of above items (1) to (11), wherein the reaction step and the deodorization step are both flow reactions in the flow passage and performed sequentially.

(13) The production method described in any one of the above items (1) to (12), wherein the deodorization step is conducted in a microreactor.

Advantageous Effects of Invention

According to the present invention, it is possible to provide a production method of industrially useful organic compounds wherein the malodorous materials generated in a reaction step can be easily and inexpensively removed, with a lower environmental burden.

Other and further features and advantages of the invention will appear more fully from the following description, appropriately referring to the accompanying drawings.

BRIEF DESCRIPTION OF THE DRAWINGS

FIG. 1 is a schematic configuration diagram showing a preferred production system for the deodorization step according to the present invention.

FIG. 2 is a schematic configuration diagram showing the total configuration of a preferred typical production system for the process from the reaction step to the deodorization step according to the present invention.

MODE FOR CARRYING OUT THE INVENTION

The production method of the present invention is a production method for producing an organic compound, in which the organic compound is an industrially useful compound. Herein, a deodorization step using a flow reaction in a flow passage is performed to remove, from a reaction liquid, a malodorous material generated or remaining in a reaction step.

The present invention is described below in detail.

As used herein, the term "industrially useful compound" produced in the present invention refers to an organic compound capable of being synthesized by organic synthesis reaction, which may be a compound for use as an industrial product or a raw material therefor.

Therefore, the production method of the present invention may be a production method including a reaction step in organic synthesis, more specifically, a production method including a reaction step for synthesizing a desired organic compound from a reactive raw material.

«Method of Producing Organic Compound»

The production method of the present invention includes at least a reaction step and a deodorization step.

In the present invention, the deodorization step may be performed after the reaction step or may be incorporated as one of sub-steps in the reaction step. It is preferable that the reaction step and the deodorization step are sequentially performed, and it is more preferable that the deodorization step is sequentially performed after the reaction step.

In the present invention, the reaction step is preferably an oxidation reaction using a sulfur atom-containing organic compound.

<Malodorous Material Generated in Reaction Step>

The malodorous material generated in the reaction step is a material that is other than the organic compound produced by the synthesis and is secondarily newly generated in the reaction step.

On the other hand, the malodorous material remaining in the reaction step is a material that is other than the organic compound produced by the synthesis and is a residue of a malodorous reaction raw material or a malodorous reaction reagent left unconsumed in the reaction.

In the present invention, removing, from the reaction liquid, a malodorous material generated in the reaction step is particularly more preferable than removing a malodorous material remaining in the reaction step, because in the former case, the working environment can be completely protected from the malodorous material.

Examples of such a malodorous material include malodorous materials associated with oxidation reaction using a sulfur atom-containing compound such as a sulfide compound or a sulfoxide compound (Swern oxidation or Corey-Kim oxidation); malodorous materials associated with alkylation using a phosphorus atom-containing compound (ionic liquid synthesis reaction); malodorous materials associated with carbon-carbon bond forming reaction using a tin atom-containing compound (Stille reaction); malodorous materials associated with α,β-unsaturated carbonylation using a selenium atom-containing compound; and malodorous materials associated with living radical polymerization using a tellurium atom-containing compound. The present invention is preferably applied to oxidation reaction using a sulfur atom-containing compound (Swern oxidation or Corey-Kim oxidation), alkylation using a phosphorus atom-containing compound (ionic liquid synthesis reaction), or carbon-carbon bond forming reaction using a tin atom-containing compound (Stille reaction); more preferably applied to oxidation reaction using a sulfur atom-containing compound. In particular, the present invention is preferably applied to removal of the odor of a sulfide compound.

Such a sulfide compound is preferably a sulfide compound represented by Formula (S).

$$R^1—S—R^2 \quad \text{Formula (S)}$$

In Formula (S), $R^1$ and $R^2$ each independently represent an alkyl group, a cycloalkyl group, or an aryl group.

The alkyl group is a linear or branched alkyl group having preferably 1 to 18 carbon atoms, more preferably 1 to 8 carbon atoms, further preferably 1 to 6 carbon atoms.

Examples of the alkyl group include methyl, ethyl, propyl, isopropyl, butyl, pentyl, hexyl, heptyl, octyl, 2-ethylhexyl, nonyl, decyl, undecyl, dodecyl, tridecyl, tetradecyl, pentadecyl, hexadecyl, heptadecyl, and octadecyl.

The cycloalkyl group is preferably a 3- to 18-membered cycloalkyl group, more preferably a 3- to 10-membered cycloalkyl group, further preferably a 3- to 7-membered cycloalkyl group, and particularly preferably a 5- or 6-membered cycloalkyl group. The number of carbon atoms of the cycloalkyl group is preferably 3 to 18, more preferably 5 to 10, further preferably 5 to 8.

Examples of the cycloalkyl group include cyclopropyl, cyclobutyl, cyclopentyl, cyclohexyl, cycloheptyl, cyclooctyl, cyclononyl, and cyclodecyl.

The number of carbon atoms of the aryl group is preferably 6 to 10. For example, the aryl group is preferably a monocyclic or bicyclic aryl group, such as phenyl and naphthyl.

Each group of these may be substituted with a substituent. Such a substituent may be a substituent with which each of the $R^3$ and $R^4$ groups in Formulas (A) and (B) below can be substituted.

In the sulfide compound represented by Formula (S), it is preferable that $R^1$ and $R^2$ each are an alkyl group. Among these, it is more preferable that the total number of carbon atoms of $R^1$ and $R^2$ is from 2 to 8.

Specific examples of the dialkyl sulfide compound having 2 to 8 carbon atoms include dimethyl sulfide, diethyl sulfide, dipropyl sulfide, diisopropyl sulfide, dibutyl sulfide, ethyl methyl sulfide, propyl methyl sulfide, isopropyl methyl sulfide, butyl methyl sulfide, butyl ethyl sulfide, butyl propyl sulfide, and butyl isopropyl sulfide. Among these, dimethyl sulfide, diethyl sulfide, dipropyl sulfide and dibutyl sulfide are preferable; and dimethyl sulfide is more preferable.

The reaction, in which the sulfide compound represented by Formula (S) is secondarily newly generated, may be an oxidation reaction that oxidizes an alcohol compound to form an aldehyde or ketone compound. Such an oxidation reaction is typically Swern oxidation or Corey-Kim oxidation. In the present invention, these oxidation reactions are preferable, and Swern oxidation is particularly preferable.

Swern oxidation is typically performed using dimethyl sulfoxide, and trifluoroacetic anhydride or oxalyl chloride as activators. On the other hand, Corey-Kim oxidation is typically performed using dimethyl sulfide and N-chlorosuccinimide as activators.

Reaction schemes are shown below, in which a desired aldehyde or ketone compound and dimethyl sulfide as a by-product are obtained by Swern oxidation using dimethyl sulfoxide, and trifluoroacetic anhydride or oxalyl chloride as activators and by Corey-Kim oxidation using dimethyl sulfide and N-chlorosuccinimide as activators.

Swern Oxidation 1

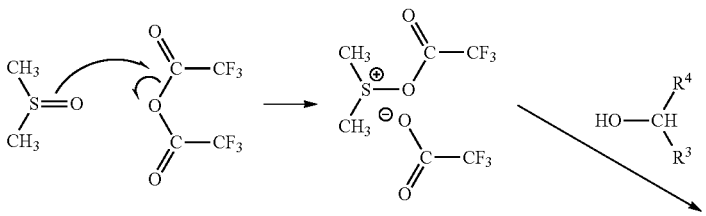

Swern Oxidation 2

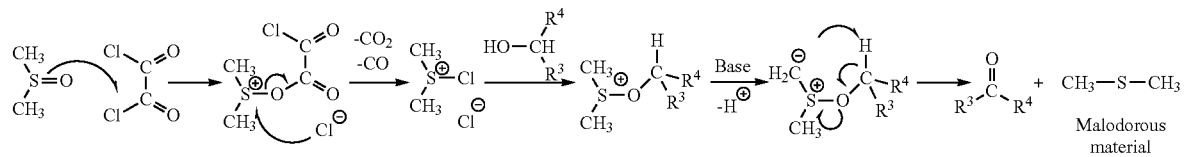

Corey-Kim Oxidation

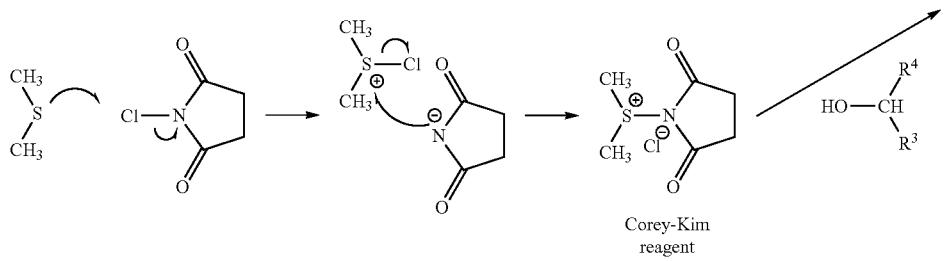

Corey-Kim reagent

Herein, $R^3$ and $R^4$ are $R^3$ and $R^4$ in Formulas (A) and (B) described below.

<Reaction Step>

The organic compound produced according to the present invention is not particularly limited if it may be any industrially useful compound, and is preferably an aldehyde or ketone compound, although.

In the present invention, the reaction is preferably an oxidation reaction, more preferably an oxidation reaction using a sulfur atom-containing organic compound.

In the present invention, the organic compound is more preferably produced by a synthetic method including subjecting an alcohol compound to an oxidation reaction.

In the present invention, the reaction step particularly preferably includes oxidizing an alcohol compound having 2 to 50 carbon atoms to form an aldehyde or ketone compound having 2 to 50 carbon atoms.

The oxidation of the alcohol compound is preferably Swern oxidation or Corey-Kim oxidation, and particularly preferably Swern oxidation.

Therefore, at least the sulfur atom-containing organic compound described above is used as an activator.

In the Swern oxidation, the sulfur atom-containing organic compound is a sulfoxide compound such as dimethyl sulfoxide. In the Corey-Kim oxidation, the sulfur atom-containing organic compound is a sulfide compound such as dimethyl sulfide.

In the Swern oxidation, a sulfoxide compound such as dimethyl sulfoxide is reduced into a sulfide compound such as dimethyl sulfide. In the Corey-Kim oxidation, some amount of a sulfide compound such as dimethyl sulfide can remain unreacted in the reaction liquid.

(Alcohol Compound as Raw Material and Aldehyde or Ketone Compound as Product)

In a preferred mode of the present invention, an alcohol compound having 2 to 50 carbon atoms is used as a raw material and oxidized to produce an aldehyde or ketone compound having 2 to 50 carbon atoms.

The alcohol compound, and the aldehyde compound or the ketone compound each is preferably a compound represented by Formula (A) or (B).

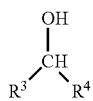

Formula (A)

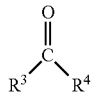

Formula (B)

In Formulas (A) and (B), $R^3$ represents a hydrogen atom, an alkyl group, a cycloalkyl group, an alkenyl group, a cycloalkenyl group, an aryl group, or a heterocyclic group. $R^4$ represents an alkyl group, a cycloalkyl group, an alkenyl group, a cycloalkenyl group, an aryl group, or a heterocyclic group. Herein, $R^3$ and $R^4$ may combine together to form a ring.

The alkyl group of $R^3$ and $R^4$ is a linear or branched alkyl group having preferably 1 to 18 carbon atoms, more preferably 1 to 12 carbon atoms.

Examples of the alkyl group include methyl, ethyl, propyl, isopropyl, butyl, pentyl, hexyl, heptyl, octyl, 2-ethylhexyl, nonyl, decyl, undecyl, dodecyl, tridecyl, tetradecyl, pentadecyl, hexadecyl, heptadecyl, and octadecyl.

The cycloalkyl group of $R^3$ and $R^4$ is preferably a 3- to 18-membered cycloalkyl group, more preferably a 3- to 10-membered cycloalkyl group, further preferably a 3- to 7-membered cycloalkyl group, and particularly preferably a 5- or 6-membered cycloalkyl group. The number of carbon atoms of the cycloalkyl group is preferably 3 to 18, more preferably 5 to 12.

Examples of the cycloalkyl group include cyclopropyl, cyclobutyl, cyclopentyl, cyclohexyl, cycloheptyl, cyclooctyl, cyclononyl, cyclodecyl, cyclododecyl, cyclododecyl, cyclotridecyl, cyclotetradecyl, cyclopentadecyl, cyclohexadecyl, cycloheptadecyl, and cyclooctadecyl.

The alkenyl group of $R^3$ and $R^4$ is a linear or branched alkenyl group having preferably 2 to 18 carbon atoms, more preferably 2 to 12 carbon atoms.

Examples of the alkenyl group include vinyl, allyl, propenyl, butenyl, pentenyl, hexenyl, heptenyl, octenyl, nonenyl, decenyl, undecenyl, dodecenyl, tridecenyl, tetradecenyl, pentadecenyl, hexadecenyl, heptadecenyl, octadecenyl, hexadienyl, dodecadienyl, octatrienyl, and tetradecatrienyl.

The cycloalkenyl group of $R^3$ and $R^4$ is preferably a 5- to 18-membered cycloalkenyl group, more preferably a 5- to 10-membered cycloalkenyl group, further preferably a 5- to 7-membered cycloalkenyl group, and particularly preferably a 5- or 6-membered cycloalkenyl group. The number of carbon atoms of the cycloalkenyl group is preferably 5 to 18, more preferably 5 to 12.

Examples of the cycloalkenyl group include cyclopentenyl, cyclohexenyl, cycloheptynyl, and cyclooctynyl.

The number of carbon atoms of the aryl group of $R^3$ and $R^4$ is preferably 6 to 14, more preferably 6 to 10. Examples thereof include a monocyclic or bicyclic aryl group, such as phenyl, tolyl, xylyl, naphthyl and phenanthryl.

The heterocyclic group of $R^3$ and $R^4$ is preferably a 5- to 18-membered heterocyclic group, more preferably a 5- to 10-membered heterocyclic group. The hetero atom constituting the heterocycle is preferably an atom selected from a nitrogen atom, an oxygen atom and a sulfur atom. The number of hetero atoms constituting the heterocycle may be 2 or more. The heterocycle of the heterocyclic group may be condensed with an aryl ring, such as a benzene ring, and a naphthalene ring; an aliphatic hydrocarbon ring, such as a cyclopentane ring, a cyclohexane ring, a cyclopentene ring, and a cyclohexene ring; a heterocycle, or the like.

Examples of the heterocyclic group include imidazolyl, oxazolyl, triazolyl, thiazolyl, 1,3,4-thiadiazolyl, pyridyl, pyrimidyl, pyrazyl, furyl, pyranyl, chromanyl, tetrahydropyranyl, thienyl, benzothiazolyl, benzoxazolyl, quinolyl, and acridinyl. Other examples thereof include 5- to 16-membered lactone rings, such as 2-oxo-oxetanyl, 2-oxo-oxolanyl, 2-oxo-chromenyl, 2-oxo-isochromenyl, 2-oxo-oxepanyl, 2-oxo-oxacyclodecanyl, 2-oxo-oxacycloundecanyl, 2-oxo-oxacyclododecanyl, 2-oxo-oxacyclotridecanyl, 2-oxo-oxacyclotetradecanyl, 2-oxo-oxacyclopentadecanyl, and 2-oxo-oxacyclohexadecanyl.

Examples of the ring formed by combining of $R^3$ and $R^4$ in combination include a saturated or unsaturated aliphatic carbon ring, and a saturated or unsaturated heterocycle. The formed ring is preferably a 3- to 18-membered ring. In the case of the heterocycle, the hetero atom constituting the heterocycle is preferably an atom selected from a nitrogen atom, an oxygen atom and a sulfur atom, and the number of hetero atoms constituting the heterocycle may be 2 or more.

Among these, the heterocycle is preferably a 5- to 18-membered ring. In the case of the lactone ring, a 4- to 18-membered ring is preferable.

Examples of the ring formed by combining of $R^3$ and $R^4$ in combination include the following rings.

1) 3- to 18-membered Saturated Ring
Monocycle

Examples thereof include a cyclopropane ring, a cyclobutane ring, a cyclopentane ring, a cyclohexane ring, a cycloheptane ring, a cyclooctane ring, a cyclononane ring, a cyclodecane ring, a cycloundecane ring, a cyclododecane ring, a cyclotridecane ring, a cyclotetradecane ring, a cyclopentadecane ring, a cyclohexadecane ring, a cycloheptadecane ring, and a cyclooctadecane ring.

Condensed Polycycle

Examples thereof include a 1,2,3,4-tetrahydronaphthalene ring, a 9,10-dihydroanthracene ring, and a tetrahydroanthracene ring.

2) 5- to 18-membered Partially Saturated Ring

Examples thereof include a cyclopropene ring, a cyclobutene ring, a cyclopentene ring, a cyclohexene ring, a cycloheptene ring, a cyclooctadiene ring, a cyclononene ring, a cyclodecene ring, a cycloundecene ring, a cyclododecatriene ring, a cyclotridecene ring, a cyclotetradecadiene ring, a cyclopentadecene ring, a cyclohexadecene ring, a cycloheptadecene ring, and a cyclooctadecene ring.

3) 4- to 18-membered Heterocycle

Examples thereof include an oxolane ring; a thiopyran ring; a crown ether ring, such as a 12-crown-4-ether ring, and a 15-crown-5-ether ring; and a lactone ring, such as a β-propiolactone ring, a γ-butyrolactone ring, and a δ-valerolactone ring.

$R^3$, $R^4$ and the ring formed by combining of $R^3$ and $R^4$ in combination may have a substituent. Such a substituent may be of any type as long as it will neither inhibit the oxidation reaction nor cause any side reaction. For example, examples of the substituent include the followings:

an alkyl group (preferably an alkyl group having 1 to 10 carbon atoms, e.g. methyl, ethyl, isopropyl, t-butyl, pentyl, heptyl, 1-ethylpentyl, 2-ethylhexyl, benzyl, 2-ethoxyethyl, or 1-carboxymethyl), an alkenyl group (preferably an alkenyl group having 2 to 20 carbon atoms, e.g. vinyl, allyl, or oleyl), an alkynyl group (preferably an alkynyl group having 2 to 20 carbon atoms, e.g. ethynyl, 2-butynyl, or phenylethynyl), a cycloalkyl group (preferably a cycloalkyl group having 3 to 20 carbon atoms, e.g. cyclopropyl, cyclopentyl, cyclohexyl, or 4-methylcyclohexyl), an aryl group (preferably an aryl group having 6 to 26 carbon atoms, e.g. phenyl, 1-naphthyl, 2-naphthyl, 4-methoxyphenyl, 2-chlorophenyl, or 3-methylphenyl), a heterocyclic group (preferably a heterocyclic group having 0 to 20 carbon atoms, of which the hetero atom constituting the ring is preferably selected from an oxygen atom, a nitrogen atom, and a sulfur atom; the group may be a 5- or 6-membered ring and condensed with a benzene ring or a heterocycle; and the heterocycle of the heterocyclic group may be a saturated ring, an unsaturated ring or an aromatic ring, e.g. 2-pyridyl, 4-pyridyl, 2-imidazolyl, 2-benzimidazolyl, 2-thiazolyl, or 2-oxazolyl), an alkoxy group (preferably an alkoxy group having 1 to 20 carbon atoms, e.g. methoxy, ethoxy, isopropyloxy, or benzyloxy), an aryloxy group (preferably an aryloxy group having 6 to 26 carbon atoms, e.g. phenoxy,1-naphthyloxy, 2-naphthyloxy, 3-methylphenoxy, or 4-methoxyphenoxy), a heterocyclic oxy group (preferably a heterocyclic oxy group of the heterocyclic group described above), an alkylthio group (preferably an alkylthio group having 1 to 20 carbon atoms, e.g. methylthio, ethylthio, isopropylthio, or benzylthio), an arylthio group (preferably an arylthio group having 6 to 26 carbon atoms, e.g. phenylthio, 1-naphthylthio, 2-naphthylthio, 3-methylphenylthio, or 4-methoxyphenylthio), an acyl group (preferably an acyl group having 20 or less carbon atoms including an alkylcarbonyl group, an alkenylcarbonyl group, an arylcarbonyl group and a heterocyclic carbonyl group, e.g. acetyl, pivaloyl, acryloyl, methacryloyl, benzoyl or nicotinoyl), an alkoxycarbonyl group (preferably an alkoxycarbonyl group having 2 to 20 carbon atoms, e.g. ethoxycarbonyl, or 2-ethylhexyloxycarbonyl), an aryloxycarbonyl group (preferably an aryloxycarbonyl group having 7 to 20 carbon atoms, e.g. phenyloxycarbonyl, or naphthyloxycarbonyl), an amino group (preferably an amino group having 0 to 20 carbon atoms including an amino group, an alkylamino group, an arylamino group, and a heterocyclic amino group, e.g. amino, N,N-dimethylamino, N,N-diethylamino, N-ethylamino, anilino, 1-pyrrolidine-1-yl, piperidine-1-yl, morpholine-1-yl, or thiomorpholine-1-yl), a sulfonamide group (preferably a sulfonamide group having 0 to 20 carbon atoms including an alkylsulfonamide group and an arylsulfonamide group, e.g. sulfonamide, N,N-dimethylsulfonamide, or N-phenylsulfonamide), a sulfamoyl group (preferably a sulfamoyl group having 0 to 20 carbon atoms including an alkylsulfamoyl group and an arylsulfamoyl group, e.g. sulfamoyl, N,N-dimethylsulfamoyl, or N-phenylsulfamoyl), an acyloxy group (preferably an acyloxy group having 1 to 20 carbon atoms, e.g. acetyloxy, or benzoyloxy), a carbamoyl group (preferably a carbamoyl group having 1 to 20 carbon atoms including an alkylcarbamoyl group and an arylcarbamoyl group, e.g. carbamoyl, N,N-dimethylcarbamoyl, or N-phenylcarbamoyl), an acylamino group (preferably an acylamino group having 1 to 20 carbon atoms, e.g. acetylamino, acryloylamino, benzoylamino, or nicotinamide), a cyano group, a nitro group, a hydroxy group, a mercapto group, a carboxy group, a sulfo group, a phosphate group, a halogen atom (e.g. fluorine atom, chlorine atom, bromine atom, or iodine atom), and an azido group ($—N_3$). Another examples thereof include an oxo group ($=O$) of a divalent group.

These substituents may be further substituted with the substituent described above.

Among these, an alkyl group, a cycloalkyl group, an alkenyl group, a cycloalkenyl group, an alkynyl group, an aryl group, a heterocyclic group, an alkoxy group, an aryloxy group, a heterocyclic oxy group, an amino group, an acyl group, an alkoxycarbonyl group, a halogen atom, an oxo group, and a group formed by the combination of these are preferable.

$R^3$ is preferably a hydrogen atom, an alkyl group having 1 to 12 carbon atoms, an alkenyl group having 2 to 12 carbon atoms, a phenyl group, a naphthyl group, or a 5- to 18-membered heterocyclic group.

$R^4$ is preferably an alkyl group having 1 to 12 carbon atoms, an alkenyl group having 2 to 12 carbon atoms, a phenyl group, a naphthyl group, or a 5- to 18-membered heterocyclic group.

Further, the ring formed by combining of $R^3$ and $R^4$ in combination is also preferable; and a 6- to 14-membered saturated ring, a 5- to 14-membered heterocycle and a 14- to 16-membered lactone ring are more preferable.

In this regard, the compounds represented by Formulas (A) and (B) may have one or more asymmetric carbon atoms depending on the substituent type, and any optical isomers, diastereoisomers, and mixtures thereof based on such asymmetric carbon atoms will also fall within the scope of the present invention.

In addition, when these compounds have one or more double bonds in the $R^3$ or $R^4$ group, any geometrical isomers based on such double bonds will also fall within the scope of the present invention.

Specific examples of the compound represented by Formula (A) are described below. However, the present invention is not limited to these examples.

The compound represented by Formula (B) may be one derived from the compound represented by Formula (A) by replacing >CH—OH by >C(=O). Therefore, examples of the compound represented by Formula (B) may be those derived from the above examples of the compound represented by Formula (A) by replacing >CH—OH by >C(=O).

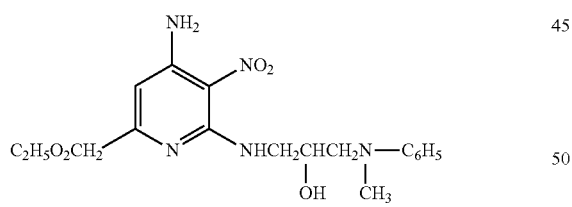

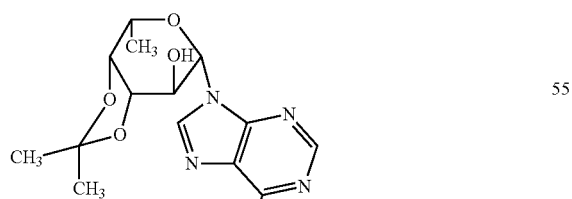

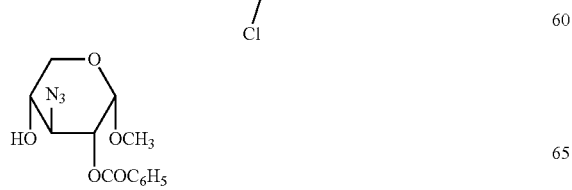

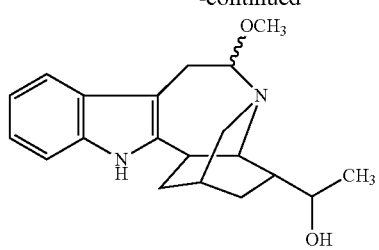

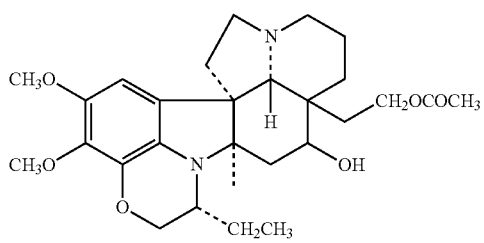

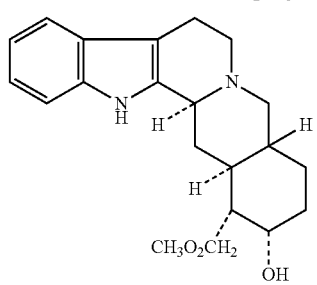

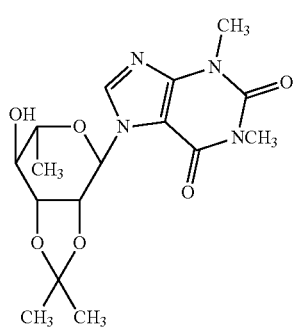

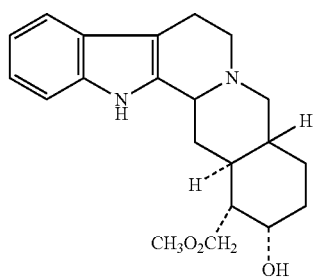

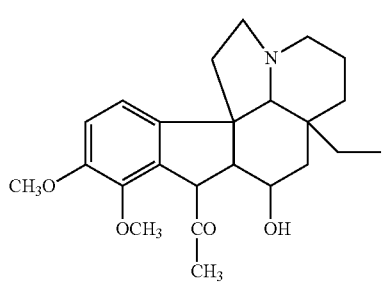

-continued
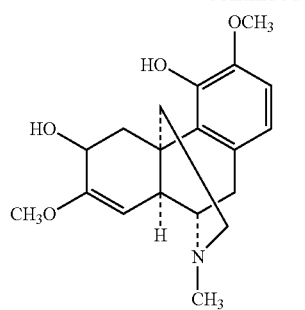
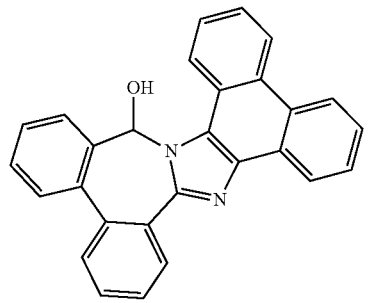
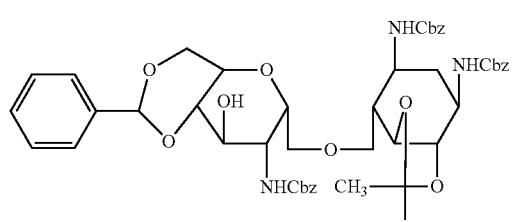
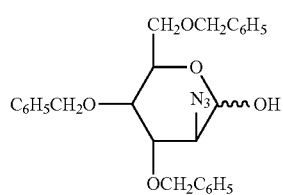
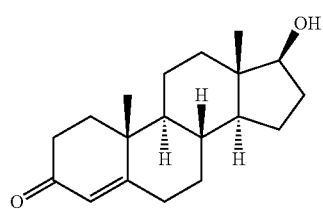
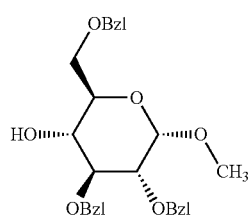
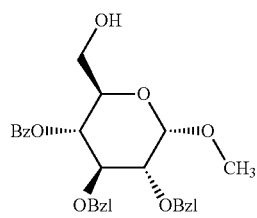
-continued
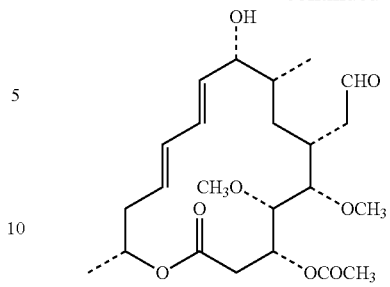
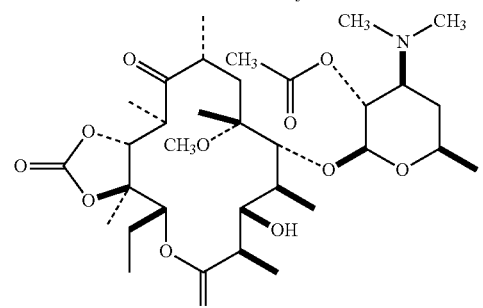
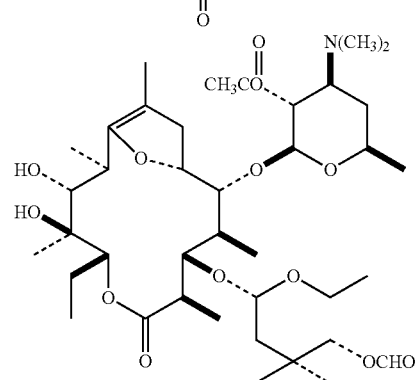
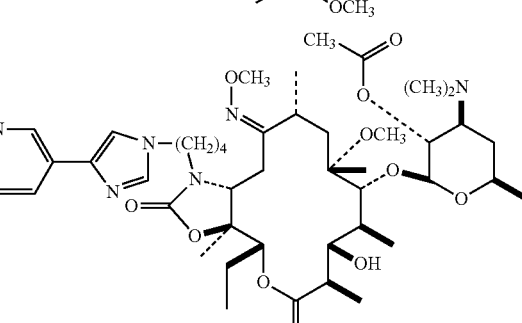
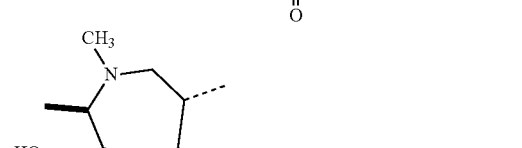
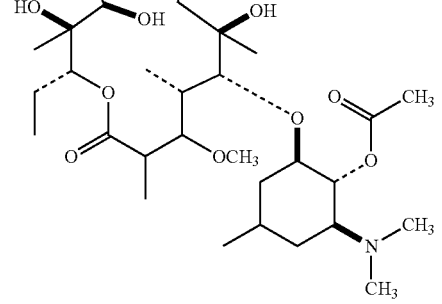

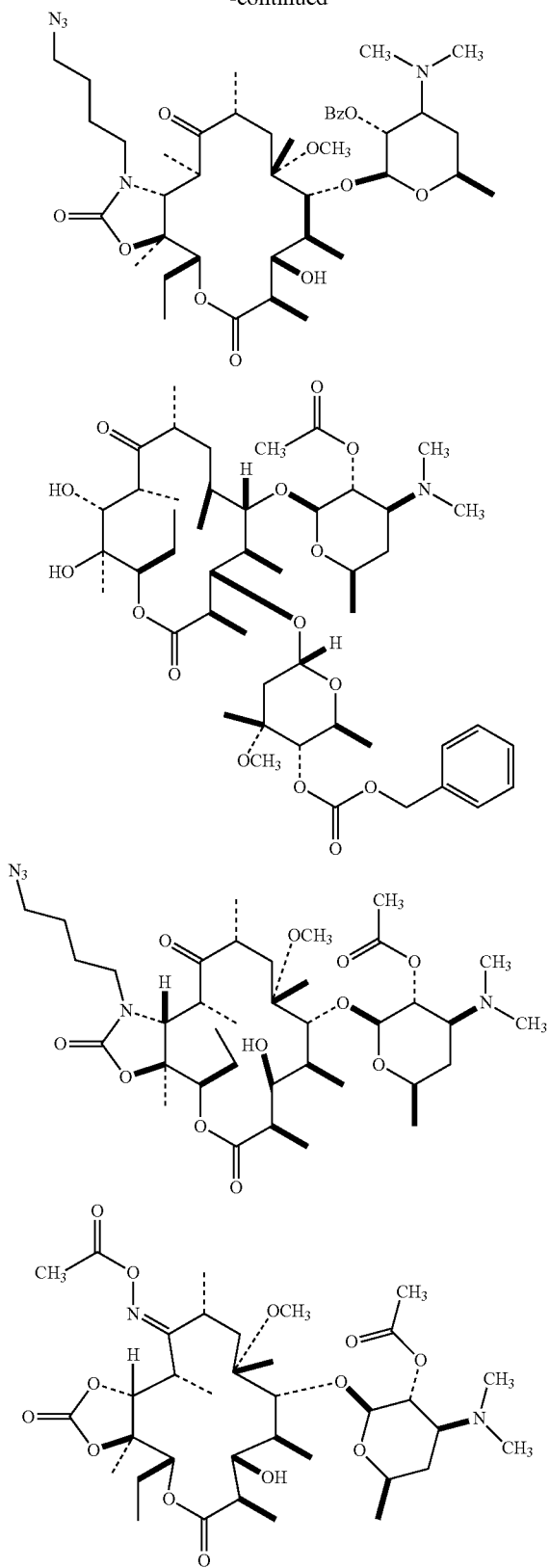

In the above, "Bz" represents a benzoyl group, "Bzl" represents a benzyl group, and "Cbz" represents a benzyloxycarbonyl group.

The compound represented by Formula (A) (alcohol compound) can be synthesized by a known method, e.g., a method described in Journal of Antibiotics, 2011, 64, 333-337; Journal of Antibiotics, 1996, 49, 493-495; Tetrahedron Letters, 2005, 46, 1483-1487; European Journal of Medicinal Chemistry, 2013, 69, 174-181; or the like.

(Activator)

In the present invention, a mixture of the compound represented by Formula (A) and an activator is particularly preferably subjected to the reaction.

Such an activator is preferably a combination of an acid anhydride or an acid halide (acid halide compound) and a sulfoxide compound, or a combination of an N-halo cyclic imide compound (N-halogenated cyclic imide compound) and a sulfide compound.

In the present invention, the combination of an acid anhydride or acid halide, and a sulfoxide compound is particularly preferable.

The sulfoxide compound is preferably a sulfoxide compound represented by Formula (SO).

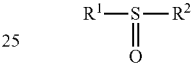

Formula (SO)

In Formula (SO), $R^1$ and $R^2$ have the same meaning as $R^1$ and $R^2$ in the sulfide compound represented by Formula (S), and preferable ranges are also the same.

Also in the case of the sulfoxide compound, it is preferable that $R^1$ and $R^2$ each are an alkyl group. Among these, it is more preferable that the total number of carbon atoms of $R^1$ and $R^2$ is from 2 to 8.

Examples of the dialkyl sulfoxide compound having 2 to 8 carbon atoms include dimethyl sulfoxide, diethyl sulfoxide, dipropyl sulfoxide, diisopropyl sulfoxide, dibutyl sulfoxide, ethylmethyl sulfoxide, propylmethyl sulfoxide, isopropylmethyl sulfoxide, butylmethyl sulfoxide, butylethyl sulfoxide, butylpropyl sulfoxide, and butylisopropyl sulfoxide. Among these, dimethyl sulfoxide, diethyl sulfoxide, dipropyl sulfoxide and dibutyl sulfoxide are preferable; and dimethyl sulfoxide is more preferable.

Various sulfoxide compounds are commercially available and can be obtained. Alternatively, the sulfoxide compound can be synthesized in accordance with a known method (e.g., a method described in Tetrahedron Lett., vol. 43, p. 5177-5179 (2002), or the like).

The acid anhydride for use in combination with the sulfoxide compound may be any of an aliphatic carboxylic acid anhydride, an aromatic carboxylic acid anhydride, a heterocyclic carboxylic acid anhydride, and any mixture of these carboxylic acid anhydrides. The acid hydride may have a chain or cyclic structure.

In the present invention, an aliphatic carboxylic acid anhydride is preferred, and a chain acid anhydride is more preferred.

The acid anhydride of the aliphatic carboxylic acid preferably has 4 to 10 carbon atoms, and may have a substituent. Such a substituent may be a substituent with which each of the $R^3$ and $R^4$ groups in Formulas (A) and (B) can be substituted. Preferably, such a substituent is a halogen atom.

Examples of the acid anhydride include acetic anhydride, butyric anhydride, isobutyric anhydride, pivalic anhydride, trifluoroacetic anhydride, heptafluoroacetic anhydride, and trichloroacetic anhydride. Among these, acetic anhydride, trifluoroacetic anhydride, and trichloroacetic anhydride are preferable; and trifluoroacetic anhydride and trichloroacetic anhydride are more preferable.

The acid halide for use in combination with the sulfoxide compound may be a carboxylic acid halide, a sulfonic acid halide, a cyanuric acid halide, a thionyl halide, a phosphorus trihalide, or a phosphorus oxyhalide.

The carboxylic or sulfonic acid may be any of an aliphatic, aromatic, or heterocyclic carboxylic or sulfonic acid.

The acid halide may also have two or more —C(=O)X or —SO$_2$X moieties, in other words, may also be a di- or poly-valent acid halide. Herein, X represents a halogen atom.

The aliphatic carboxylic acid for the aliphatic carboxylic acid halide is preferably an alkane carboxylic acid, which preferably has 1 to 10 carbon atoms, more preferably has 2 to 7 carbon atoms. The aromatic carboxylic acid for the aromatic carboxylic acid halide preferably has 6 to 10 carbon atoms, more preferably 6 or 7 carbon atoms. Such an aromatic carboxylic acid may be benzenecarboxylic acid or naphthalenecarboxylic acid. The heterocycle of the heterocyclic carboxylic acid halide is preferably one represented by $R^3$ or $R^4$ in Formula (A) or (B). The number of carbon atoms of the acid halide of a heterocyclic carboxylic acid is preferably 2 to 7.

The aliphatic sulfonic acid for the aliphatic sulfonic acid halide is preferably an alkane sulfonic acid, which preferably has 1 to 10 carbon atoms, more preferably has 2 to 7 carbon atoms. The aromatic sulfonic acid for the aromatic sulfonic acid halide preferably has 6 to 10 carbon atoms, more preferably 6 or 7 carbon atoms. Such an aromatic sulfonic acid may be benzenesulfonic acid or naphthalenesulfonic acid. The heterocycle of the heterocyclic sulfonic acid halide is preferably one represented by $R^3$ or $R^4$ in Formula (A) or (B). The number of carbon atoms of the acid halide of a heterocyclic sulfonic acid is preferably 2 to 7.

In the present invention, the acid halide is preferably an acid halide of a monovalent or divalent aliphatic carboxylic acid, an acid halide of an aromatic carboxylic acid, an acid halide of an aromatic carboxylic acid, an acid halide of an aliphatic sulfonic acid, a halide of cyanuric acid, a thionyl halide, a phosphorus trihalide, and a phosphorus oxyhalide.

Further, the number of carbon atoms of the acid halide is preferably 2 to 7, as described above.

The acid halide is preferably an acid chloride or an acid bromide, and particularly preferably an acid chloride.

Preferred examples of the acid chloride include oxalyl chloride, cyanuric chloride, benzoyl chloride, methanesulfonyl chloride, thionyl chloride, phosphorus trichloride, phosphorus oxychloride, and acetyl chloride. Among these, oxalyl chloride is particularly preferable.

The amount of the sulfoxide compound to be used is preferably 1.0 to 5.0 molar equivalents, more preferably 1.5 to 4.5 molar equivalents, further more preferably 2.0 to 4.0 molar equivalents, based on the amount of the raw material alcohol compound.

The amount of the acid anhydride or acid halide to be used is preferably 1.0 to 3.0 molar equivalents, more preferably 1.1 to 2.8 molar equivalents, further more preferably 1.2 to 2.5 molar equivalents, based on the amount of the raw material alcohol compound.

In the present invention, the sulfoxide compound may be mixed in advance with the acid anhydride or the acid halide, and the resulting mixture may be mixed with the raw material alcohol compound. Alternatively, the sulfoxide compound, the acid anhydride or the acid halide, and the raw material alcohol compound may be mixed simultaneously.

The sulfide compound represented by Formula (S) described above is preferably used in the Corey-Kim oxidation.

The N-halo cyclic imide compound for use in combination with the sulfide compound preferably has a 5- or 6-membered imide ring, more preferably a 5-membered imide ring. Examples of the imide ring include succinimide, hexahydrophthalimide, 2,2-dimethylsuccinimide, 2-ethyl-2-methylsuccinimide, methyleneglutarimide, 3,3-dimethylglutarimide, 3-ethyl-3-methylglutarimide, and 3,3-tetramethyleneglutarimide. Among these, succinimide is particularly preferable. The halogen atom at the N-position is preferably a chlorine atom or a bromine atom, more preferably a chlorine atom. As the N-halo cyclic imide compound, N-chlorosuccinimide is particularly preferable.

The amount of the sulfide compound to be used is preferably 1.0 to 5.0 molar equivalents, more preferably 1.2 to 4.0 molar equivalents, further more preferably 1.5 to 3.0 molar equivalents, based on the amount of the raw material alcohol compound.

The amount of the N-halo cyclic imide compound to be used is preferably 1.0 to 4.0 molar equivalents, more preferably 1.2 to 3.3 molar equivalents, further more preferably 1.5 to 2.5 molar equivalents, based on the amount of the raw material alcohol compound.

The sulfide compound may be mixed in advance with the N-halo cyclic imide compound, and the resulting mixture may be mixed with the raw material alcohol compound. Alternatively, the sulfide compound, the N-halo imide compound, and the raw material alcohol compound may be mixed simultaneously. In a preferred mode of the present invention, the sulfide compound is mixed in advance with the N-halo cyclic imide compound, and the resulting mixture is mixed with the raw material alcohol compound.

(Base)

A base is used in the reaction between the raw material alcohol compound and the activator. The base is preferably pyridine or a tertiary amine compound, more preferably a tertiary amine compound.

The tertiary amine compound may be an aliphatic, aromatic, or heterocyclic tertiary amine compound. A cyclic tertiary amine compound may also be used.

The nitrogen atom may be substituted with an aliphatic group substituent. In this case, the aliphatic group is preferably an alkyl group or a cycloalkyl group. In the case of the alkyl group, the alkyl group preferably has 1 to 18 carbon atoms. In the case of the cycloalkyl group, preferred thereof include cyclopentyl and cyclohexyl, and the cycloalkyl group preferably has 5 to 18 carbon atoms.

The nitrogen atom may be substituted with an aromatic group substituent. In this case, the aromatic group preferably has 6 to 18 carbon atoms, and examples of the aromatic group include a phenyl group and a naphthyl group.

The nitrogen atom may also be substituted with a heterocyclic group substituent. In this case, the heterocyclic group is preferably one exemplified as $R^3$ or $R^4$ in Formula (A) or (B).

Two or three substituents on the nitrogen atom may be combined together to form a ring. Such a ring is preferably a 5- or 6-membered ring. Such a ring may be fused with any other ring. Such a ring may also be a cross-linked ring. Examples thereof include a pyrrolidine ring, a piperazine ring, a morpholine ring, a thiomorpholine ring, a quinuclidine ring, and a 1,4-diazabicyclo[2.2.2]octane ring (DABCO).

Various tertiary amine compounds are commercially available and can be easily obtained.

Examples of the tertiary amine compound include trimethyl amine, dimethyl ethyl amine, diethyl methyl amine, triethyl amine, diethyl methyl amine, dimethyl isopropyl amine, dipropyl ethyl amine, diisopropyl ethyl amine, butyl dimethyl amine, butyl diisopropyl amine, tributyl amine, triisobutyl amine, triamyl amine, triisoamyl amine, cyclohexyl dimethyl amine, dicyclohexyl methyl amine, cyclohexyl diethyl amine, dicyclohexyl ethyl amine, butyl dicyclohexyl amine, triheptyl amine, dimethyl octyl amine, methyl dioctyl amine, trioctyl amine, tris(2-ethylhexyl) amine, trinonyl amine, dimethyl decyl amine, tridecyl amine, triundecyl amine, dimethyl dodecyl amine, didodecyl methyl amine, tridodecyl amine, dimethyltetradecyl amine, dimethyl hexadecyl amine, dimethyl octadecyl amine, dioctadecyl methyl amine, N-methylmorpholine, N-ethylmorpholine, quinuclidine, and 1,4-diazabicyclo[2.2.2]octane.

Among these, triethyl amine, diisopropyl ethyl amine, dicyclohexyl methyl amine, and cyclohexyl diethyl amine are preferable.

The amount of the base to be used is preferably 1.2 to 6.0 molar equivalents, more preferably 1.3 to 5.5 molar equivalents, further more preferably 1.5 to 5.0 molar equivalents, based on the amount of the raw material alcohol compound.

After the raw material alcohol compound and the activator are mixed, the base may be mixed with the resulting mixture. Alternatively, the base, the raw material alcohol compound, and the activator may be mixed at the same time. It is preferable that the raw material alcohol compound and the activator are mixed, and then the base is mixed with the resulting mixture.

(Reaction Solvent)

The reaction solvent may be any type capable of dissolving the substrate and not undergoing any side reaction.

A single solvent or a mixture of two or more solvents may be used.

Examples of the reaction solvent include a ketone-series solvent, such as acetone, ethyl methyl ketone, methyl isopropyl ketone, diisopropyl ketone, methyl isobutyl ketone, and diisobutyl ketone; an ether-series solvent, such as diethyl ether, diisopropyl ether, methyl-tert-butyl ether, tetrahydrofuran (THF), and dioxane; an amide-series solvent, such as dimethylformamide, dimethylacetamide, N-methyl-2-pyrolidone, tetramethylurea, and 1,3-dimethyl imidazolinone; a sulfur-containing solvent, such as dimethyl sulfoxide and sulfolane; a nitrile-series solvent, such as acetonitrile; a glycol-series solvent, such as ethylene glycol dimethyl ether, propylene glycol diethyl ether, diethylene glycol dimethyl ether, diethylene glycol ethyl methyl ether, ethylene glycol diacetate, ethylene glycol distearate, ethylene glycol diacrylate, and diethylene glycol diacetate; a halogen-series solvent, such as methylene chloride, chloroform, and chlorobenzene; an ester-series solvent, such as methyl acetate, ethyl acetate, isopropyl acetate, and butyl acetate; an aromatic hydrocarbon-series solvent, such as toluene, xylene, mesitylene, and tetrahydronaphthalene; and a terpene-series solvent, such as terpinene, terpinolene, cymene, and phellandrene.

Among these, acetone, THF, acetonitrile, methylene chloride, ethyl acetate, and toluene are preferable.

The amount of the solvent to be used is generally 1 to 300 mL, preferably 1 to 150 mL, more preferably 5 to 100 mL, based on 1 g of the raw material alcohol compound, through it depends on the substrate and the reaction conditions.

<Reaction Temperature and Reaction Time in Reaction Step>

The reaction step may be performed in a batch method under normal conditions (e.g., see Jikken Kagaku Koza (Handbook of Experimental Chemistry), 4th ed., volume 23, 1991, published by Maruzen Company Ltd.).

When the reaction is performed as a flow reaction, the reaction temperature is preferably −30 to 60° C., more preferably −25 to 50° C., further more preferably −20 to 40° C. In the flow reaction, the mixing temperature is preferably −30 to 40° C., more preferably −20 to 30° C. In the flow reaction, the reaction time is preferably 0.001 to 60 seconds, more preferably 0.005 to 50 seconds, further more preferably 0.01 to 40 seconds, particularly more preferably 0.02 to 30 seconds.

The raw material alcohol compound, the activator, the individual components of the activator, and the base may be each dissolved in the solvent and then mixed together, or may be mixed as they are without being dissolved in the solvent.

In the reaction step, the reaction may be performed in a batch method or as a flow reaction in a flow passage.

In the present invention, the reaction is preferably performed as a flow reaction in the same flow passage as that for the deodorization step, and, in particular, preferably performed in a microreactor.

<Deodorization Step>

The method of removing the odor of the malodorous material may be a method including converting the malodorous material into a quaternary salt as a water-soluble compound using methyl halide or other materials and removing the water-soluble compound; or a method of removing the odor of the malodorous material by oxidation reaction using an oxidizing agent. Preferred method is a method of removing the odor of the malodorous material by oxidation reaction.

The oxidizing agent may be arbitrarily selected. A wide variety of oxidizing agents is commercially available and can be easily obtained. Examples of the oxidizing agent include oxo acids of halogen (or salts thereof), including hypochlorous acid or salts thereof, organic peroxides, inorganic peroxides, halogenating agents, hypervalent iodine compounds, N-oxide compounds, and nitroxyl radical (>N.) compounds.

In the present invention, the oxidizing agent is preferably liquid or soluble in the solvent because the deodorization step is performed using a flow reaction in a flow passage.

However, if the oxidizing agent is solid and insoluble in the solvent, the oxidizing agent may be charged in the flow passage, and the liquid may be passed through the flow passage to undergo oxidation reaction.

In the present invention, the odor of the malodorous material is removed using a flow reaction in a flow passage, which makes it possible to efficiently and selectively remove the malodorous material in a short time, in other words, makes it possible to convert the malodorous material into a non-malodorous material. Therefore, the malodorous material can be selectively converted into a non-malodorous material even if the organic compound obtained in the reaction step has an unstable or reactive functional group, such as a double bond, an ester bond (—OC(=O)—), an amino group, an azido group (—$N_3$), a hydroxy group, an acyloxy group, a benzyloxy group, a nitro group, a formyl group, or an acyl group.

A reaction scheme is shown below, in which hypochlorous acid (HOCl) is used to convert a sulfide compound, a malodorous material, into a sulfone compound. Herein, $R^1$ and $R^2$ have the same meaning as those in Formula (S).

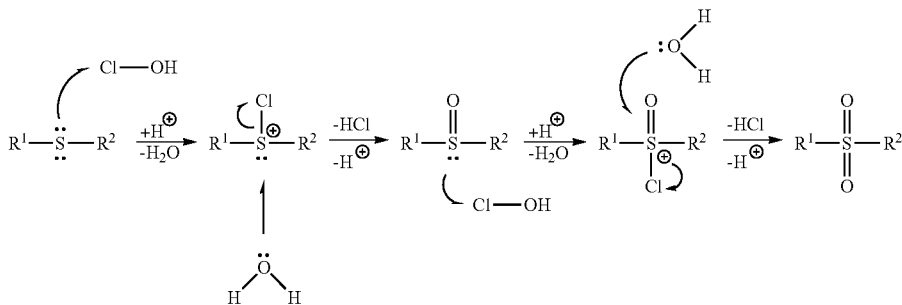

The oxo acid (or a salt thereof) of the halogen is preferably oxo acid (or a salt thereof) of chlorine, and specific examples thereof include perchloric acid, hypochlorous acid, chlorous acid and chloric acid (or a salt of these). Among these, hypochlorous acid, chlorous acid or chloric acid (or a salt of these) is preferable; and a hypochlorous acid salt aqueous solution is particularly preferable.

Specific examples of the organic peroxide include benzoyl peroxide, tert-butyl hydroperoxide, bis(trimethylsilyl) peroxide, 3-chloroperoxybenzoic acid, cumene hydroperoxide, di-tert-butyl peroxide, peracetic acid/acetic acid solution, and peracetic acid/hydrogen peroxide solution. Among these, peracetic acid/acetic acid solution and peracetic acid/hydrogen peroxide solution are preferable, and peracetic acid/hydrogen peroxide solution is particularly preferable.

A specific example of the inorganic peroxide includes hydrogen peroxide solution.

Examples of the hypervalent iodine compound include 1-acetoxy-5-bromo-1,2-benziodoxol-3(1H)-one, [bis(trifluoroacetoxy)iodo]benzene, [bis(trifluoroacetoxy)iodo]pentafluorobenzene, 1-(tert-butylperoxy)-1,2-benziodoxol-3(1H)-one, bis(pyridine)iodonium tetrafluoroborate, Dess-Martin periodinane, iodosobenzene, 2-iodosobenzoic acid, iodobenzene diacetate, 2-iodoxybenzoic acid, and [hydroxy(tosyloxy)iodo]benzene.

Examples of the halogenating agent include N-chlorosuccinimide, N-bromosuccinimide, N-chlorophthalimide, N-bromophthalimide, 1,3-dichloro-5,5-dimethylhydantoin, 1,3-dibromo-5,5-dimethylhydantoin, trichloroisocyanuric acid, tribromoisocyanuric acid, N-iodosuccinimide, and 1,3-diiodo-5,5-dimethylhydantoin. Among these, N-chlorosuccinimide, N-bromosuccinimide, 1,3-dichloro-5,5-dimethylhydantoin, and 1,3-dibromo-5,5-dimethylhydantoin are preferable; and N-chlorosuccinimide and 1,3-dichloro-5,5-dimethylhydantoin, which are low-priced, are more preferable.

Examples of the N-oxide compound include 2,6-dichloropyridine-N-oxide, 4-(dimethylamino)pyridine-N-oxide hydrate, 2,6-lutidine-N-oxide, 4-methylmorpholine-N-oxide, pyridine-N-oxide, trimethylamine-N-oxide dihydrate, and trimethylamine-N-oxide anhydride.

The nitroxyl radical compound is preferably a 5- or 6-membered compound, more preferably a compound in which both substituent carbon atoms on the nitrogen atom of >N—O. form two alkyl groups (preferably methyl groups), further more preferably a compound having a 2,2,6,6-tetramethylpiperidin-1-oxyl (TEMPO) skeleton.

Examples of the compound having a TEMPO skeleton include 4-acetylamino-TEMPO, 4-benzoyloxy-TEMPO, 4-[2-[2-(4-iodophenoxy)ethoxy] carbonyl]benzoyloxy-2,2,6,6-tetramethylpiperidin-1-oxyl, 4-methoxy-TEMPO, and TEMPO.

In the present invention, the oxidizing agent is preferably selected from hypochlorous acid or a salt thereof, a halogenating agent, and peracetic acid.

These oxidizing agents are liquid and suitable for the flow reaction in the flow passage. Using any of these oxidizing agents, the malodorous material can be very selectively converted into a non-malodorous material even if the organic compound obtained in the reaction step has an unstable or reactive functional group.

The amount of the oxidizing agent to be used is preferably 0.5 to 5.0 molar equivalents, more preferably 1.0 to 5.0 molar equivalents, further more preferably 1.1 to 4.5 molar equivalents, particularly preferably 1.2 to 4.0 molar equivalents, based on the amount of the acid anhydride or the acid halide to be used in the reaction step.

The solvent for use in the deodorization step may be the same or different from the solvent for use in the reaction step described above.

The amount of the solvent to be used may be the same as that in the reaction step described above, though it depends on the substrate and reaction conditions.

The solvent may be further added to the reaction liquid obtained in the reaction step. In the present invention, however, the reaction liquid obtained in the reaction step is preferably subjected as it is to the flow reaction in the flow passage. The solvent further added to the reaction liquid obtained in the reaction step may be the same as or different from the solvent in the reaction step.

The oxidizing agent may be dissolved in the solvent and then mixed with the reaction liquid obtained in the reaction step. Alternatively, only the oxidizing agent may be mixed with the reaction liquid obtained in the reaction step.

In the present invention, the reaction temperature in the deodorization step is preferably from −20 to 60° C., more preferably from −10 to 55° C., further more preferably from −5 to 50° C., and particularly preferably from 0 to 40° C.

In the present invention, the time for which the deodorization step is retained in the flow passage (reaction time) is preferably 0.01 to 120 seconds, more preferably 0.01 to 60 seconds, further more preferably 0.05 to 50 seconds, particularly preferably 0.1 to 40 seconds, most preferably 0.2 to 30 seconds.

When the flow reaction in the flow passage is performed using a microreactor, the flow passage of the micromixer (e.g., FIG. 1 shows flow passages between points 3 and 5, between points 4 and 5, and immediately downstream of point 5, respectively) may have any inner diameter or any cross-sectional area. In the present invention, however, the inner diameter (cross-sectional area) of the flow passage is preferably 0.05 to 5.0 mm (0.00196 to 19.6 mm$^2$), more preferably 0.10 to 2.5 mm (0.00785 to 4.9 mm$^2$), further more preferably 0.15 to 1.5 mm (0.018 to 1.8 mm$^2$).

In this regard, the cross-sectional shape of the flow passage described above may be circular or square.

<Reactor>

In the present invention, the reaction in the reaction step described above may be performed in a batch method or as a flow reaction in a flow passage, whereas the deodorization step is performed using a flow reaction in a flow passage.

The flow reaction in the flow passage may be of any type. In particular, the flow reaction in the flow passage is preferably performed using a microreactor.

The microreactor has very small flow passages capable of mixing a plurality of liquids. If necessary, the microreactor may have feed passages that communicate with the flow passages to feed liquids to the flow passages. If necessary, the microreactor may further have components other than the flow passages and the feed passages.

The microreactor for use in the present invention is not particularly limited as long as it has very small flow passages capable of mixing a plurality of liquids. The microreactor may be appropriately selected, depending on the purpose, for example, from a micromixer (such as a substrate type micromixer or a joined pipe micromixer) and a branched tube.

The substrate type micromixer, which is sometimes called a microchannel, is composed of a substrate and flow passages formed inside the substrate or on the surface of the substrate.

The substrate type micromixer may be of any type as long as the effect of the present invention is not impaired. The substrate type micromixer may be appropriately selected, depending on the purpose, from, for example, the mixer described in WO 96/30113 A having very small flow passages for mixing; and the mixer described in W. Ehrfeld, V. Hessel, H. Lowe, "Microreactors," Chapter 3, published by Wiley-VCH.

Besides the flow passages described above, the substrate type micromixer preferably has feed passages that communicate the flow passages to feed a plurality of liquids to the flow passages. In other words, the micromixer preferably has a structure in which the upstream side of the flow passage described above is branched depending on the number of feed passages.

The number of feed passages is not particularly limited, and can be appropriately selected depending on the purpose. Preferably, a plurality of liquids to be mixed are fed from separate feed passages and joined and mixed together in the flow passage. Alternatively, the micromixer may be so configured that one liquid can be previously charged into a flow passage, and another liquid can be fed from a feed passage to the flow passage.

The joined pipe micromixer has flow passages formed in the interior and optionally connection means for connecting tubes to the flow passages formed in the interior. The connection means is not particularly limited, and can be appropriately selected depending on the purpose from known tube connection types, such as a screw type, a union type, a butt weld type, a socket welding type, a socket weld type, a flange type, a bite type, a flare type, and a mechanical type.

Besides the flow passages described above, feed passages that communicate the flow passages to feed a plurality of liquids to the flow passages are preferably formed in the interior of the joined pipe micromixer. In other words, the micromixer preferably has a structure in which the upstream side of the flow passage described above is branched depending on the number of feed passages. When two feed passages are provided, the joined pipe micromixer may be of, for example, T-shaped or Y-shaped. When three feed passages are provided, the joined pipe micromixer may be, for example, cruciform. Alternatively, the micromixer may be so configured that one liquid can be previously charged into a flow passage, and another liquid can be fed from a feed passage to the flow passage.

The material of the micromixer is not particularly limited, and can be appropriately selected depending on requirements such as heat resistance, pressure resistance, solvent resistance, and easy workability. Examples of the material of the micromixer include metals or alloys including stainless steel, titanium, copper, nickel, aluminum, and Hastelloy (registered trademark), silicone, fluororesins such as Teflon (registered trademark) and PFA (perfluoroalkoxy resin), and TFAA (trifluoroacetamide).

The micromixer is configured to accurately control the flow of the reactant solution by means of its microstructure. Therefore, the micromixer is preferably manufactured by micro-machining technology.

Any micro-machining technology is not particularly limited, and can be appropriately selected depending on the purpose, for example, from (a) LIGA technology using X-ray lithography in combination with electroplating, (b) high aspect ratio photolithography using EPON-SU8, (c) mechanical micro-cutting (e.g., micro-drill processing with a high speed rotatable drill with a diameter of the order of a micrometer), (d) high aspect ratio processing of silicon using deep RIE, (e) hot embossing, (f) optical shaping, (g) laser processing, and (h) ion beam techniques.

The micromixer may be any of commercially available micromixers such as a microreactor having an interdigital channel structure, a single mixer and a caterpillar mixer manufactured by Institut für Mikrotechnik Mainz GmbH (IMM), Micro Glass Reactor manufactured by Mikroglas GmbH, CYTOS manufactured by CPC Systems GmbH, YM-1 Mixer and YM-2 Mixer manufactured by Yamatake Co., Ltd., Mixing Tee and Tee (T-shaped connector) manufactured by SHIMADZU GLC Ltd., IMT Chip Reactor manufactured by Institute of Microchemical Technology Co., Ltd., Micro Hi-Mixer developed by Toray Engineering Co., Ltd., Union Tee manufactured by Swagelok Company, a mixer manufactured by YMC CO., LTD., and a mixer manufactured by Nakamura Choukou Co., Ltd.

Any of these micromixers may be used alone as a microreactor, or a tube reactor may be connected to the downstream part of any of these micromixers to form an extended flow passage. The length of the flow passage can be adjusted by connecting a tube reactor to the downstream part of the micromixer.

The time of retention of the mixed liquid (reaction time) is proportional to the length of the flow passage.

In this regard, the tube reactor is a reactor for accurately controlling the time required for solution to undergo reaction (retention time control) after the solution is prepared by quick mixing by the micromixer.

The tube reactor is not particularly limited. For example, the inner diameter, outer diameter, length, material, and other features of the tube may be appropriately selected depending on the desired reaction.

The tube reactor may be any of commercially available products, such as a stainless steel tube manufactured by GL Sciences Inc. (outer diameter 1/16 inches (1.58 mm), inner diameter selectable from 250 μm, 500 μm, 800 μm, and 1,000 μm, 1/8 inches (3.17 mm), with the tube length adjustable by the user).

The material of the tube reactor is not limited, and any of the above examples of the material of the micromixer is preferably used to form the tube reactor.

The flow passage described above has the functions of mixing a plurality of liquids by diffusion and removing heat of reaction.

The method of mixing the liquids in the flow passage described above is not particularly limited, and can be appropriately selected depending on the purpose, for example, from laminar mixing and turbulent mixing. In particular, laminar mixing (static mixing) is preferred because it allows more efficient reaction control or heat removal. Since the flow passage of the microreactor is very small, a plurality of liquids fed from the feed passages tends to spontaneously form dominantly laminar flows so that they are diffused and mixed in directions perpendicular to the flows. For laminar mixing, branch and meeting points may be provided in the flow passage to divide the laminar flow cross-section of the liquid, so that the mixing rate can be increased.

Turbulent mixing (dynamic mixing) may be provided in the flow passage of the microreactor. In this case, laminar flow can be changed to turbulent flow by controlling the flow rate and the geometry of the flow passage (such as the three-dimensional shape of the liquid contact portion, the bending of the flow passage, or other shapes, or the wall surface roughness). Turbulent mixing has advantage in that it can provide higher mixing efficiency and higher mixing rate than laminar mixing.

In this regard, the inner diameter, the cross-sectional area, length, and cross-sectional shape of the flow passage are not particularly limited and can be appropriately selected depending on the purpose.

While the flow passage of the micromixer has been described above, the flow passage of the reactor preferably has a cross-sectional area of 0.00196 to 19.6 mm$^2$. The cross-section may have any shape as long as it has such a cross-sectional area.

The feed passages have the functions of communicating with the flow passage described above and feeding a plurality of liquids to the flow passage. In general, other sides of the feed passages than their sides communicating with the flow passage described above are connected to containers containing the liquids to be mixed.

The feed passages may have any inner diameter as long as the effect of the present invention is not impaired. The inner diameter of the feed passages can be appropriately selected depending on the purpose.

When the microreactor has a plurality of feed passages, they may have the same or different inner diameters.

Components other than the flow passages and the feed passages described above are not particularly limited and can be appropriately selected depending on the purpose. Such components include, for example, a pump for use in liquid feeding, temperature control means, reaction acceleration means, a sensor, and a tank for storing the produced compound.

The pump is not particularly limited, and can be appropriately selected from industrially useful pumps. Pumps free of pulsation during liquid feeding are preferred, such as plunger pumps, gear pumps, rotary pumps, and diaphragm pumps.

The temperature control means is not particularly limited and can be appropriately selected depending on the reaction temperature. Examples of the temperature control means include a thermostatic chamber, a circulator, a heat exchanger, and a backpressure valve.

The reaction acceleration means can be appropriately selected depending on the liquids to be mixed or the desired reaction. Examples of the reaction acceleration means include vibrational energy applying means, heating means, light irradiation means, and voltage applying means. The microreactor having voltage applying means may be, for example, the micro-flow electrochemical reactor disclosed in JP-A-2006-104538.

The sensor is not particularly limited, and examples thereof include a temperature sensor, a flow rate sensor, and a pressure sensor for measuring the pressure in the flow passage.

A plurality of raw materials may be supplied at the same or different flow rates to the microreactor. The pump for use in liquid feeding may be any industrially useful liquid feed pump. Preferably, the pump is of a type that can be as free as possible of pulsation during liquid feeding. The pump is preferably a plunger pump, a gear pump, a rotary pump, a diaphragm pump or the like.

In the microreactor, liquid or solution-state compounds are mixed and reacted by the kinetic energy of the flowing liquid and solution. If necessary, however, energy for accelerating mixing, such as vibrational energy, may be applied from outside the microreactor. The mixing can be changed from static mixing (laminar flow) to dynamic mixing (turbulent flow) according to the flow rate and the geometry of the reactor (such as the three-dimensional shape of the liquid contact portion, the bending of the flow passage, or other shapes, or the wall surface roughness). The mixing may be any of turbulent mixing and laminar mixing.

Hereinafter, a preferred reactor according to the present invention will be described with reference to FIGS. 1 and 2.

FIG. 1 is a schematic configuration diagram showing a preferred production system for the deodorization step according to the present invention, and FIG. 2 is a schematic configuration diagram showing the total configuration of a preferred production system for the process from the reaction step to the deodorization step according to the present invention.

In this case, the reaction step shown in FIG. 2 is based on Swern oxidation or Corey-Kim oxidation. It will be understood that the reaction is not limited to Swern oxidation or Corey-Kim oxidation and solutions A and B are also not limited to solutions containing such compounds. These drawings merely show the schematic configuration of typical examples.

Hereinafter, FIGS. 1 and 2 will be briefly described.

In FIG. 1, solution A is a solution containing a malodorous material, and solution B is a solution containing an oxidizing agent. Moreover, points 1 and 2 each are a port for supplying a raw material to the microreactor. Points 3 and 4 each are a port for supplying a raw material to the micromixer. Point 5 is a start point of mixing of the solutions A and B. Point 6 is the exit of the microreactor. In this case, section 1 to 3 (a section between points 1 and 3) is a section for controlling the temperature of solution A, section 2 to 4 (a section between points 2 and 4) is a section for controlling the temperature of solution B, and section 5 to 6 (a section between points 5 and 6) is a section for the reaction between solutions A and B.

In FIG. 2, solution A1 is a solution containing an alcohol compound, and a sulfoxide compound or a sulfide compound, and solution A2 is a solution containing an acid anhydride or an N-halo cyclic imide compound. Solution A3 is a solution containing a base, and solution B is a solution containing an oxidizing agent, which is the same as solution B in FIG. 1. It will be understood that the solutions for use in the present invention are not limited to solutions A1 to A3 and B and that the compounds to be added to the respective solutions are not limited to those shown in the drawings.

Points 7 to 10 are each a port for supplying a raw material to the microreactor. Points 11, 13, 14, 16, 17, and 19 are each a port for supplying a raw material to the micromixer. Point 12 is a mixing start point in a first step (a reaction between solutions A1 and A2). Point 15 is a mixing start point in a second step (a reaction with solution A3). Point 18 is a mixing start point in a third step (a reaction with solution B). Point 20 is the exit of the microreactor. The solution corresponding to solution A in FIG. 1 is supplied from point 17.

In this case, section 7 to 11 (a section between points 7 and 11) is a section for controlling the temperature of solution A1. Section 8 to 13 (a section between points 8 and 13) is a section for controlling the temperature of solution A2. Section 9 to 16 (a section between points 9 and 16) is a section for controlling the temperature of solution A3. Section 10 to 19 (a section between points 10 and 19) is a section for controlling the temperature of solution B. Moreover, section 12 to 14 (a section between points 12 and 14) is a section for the reaction in the first step. Section 15 to 17 (a section between points 15 and 17) is a section for the reaction in the second step. Section 18 to 20 (a section between points 18 and 20) is a section for the reaction in the third step.

The aldehyde or ketone compound obtained by the production method of the present invention can be isolated by a known method. For example, the aldehyde or ketone compound is isolated and purified using, as needed, one or any appropriate combination of extraction with an organic solvent, distillation, reprecipitation with an organic solvent, water, or a mixture of an organic solvent and water, crystallization, and column chromatography.

EXAMPLES

The present invention will be described in more detail based on examples given below, but the invention is not meant to be limited by these.

The structure of the synthesized product was identified by NMR, IR, and milli-mass spectroscopy.

The reaction rate to the desired product was determined by analyzing the content from the peak area ratio using high performance liquid chromatography (HPLC).

The HPLC measurement was performed under the following conditions: column, Waters XBridge C18; eluent, acetonitrile/water (V/V=7/3); buffer, 0.1% phosphoric acid; detector, UV 210 to 254 nm Corona CAD or RI; flow rate, 1.0 mL/min; column temperature, 30 to 40° C.

The isolation yield of the product for which no standard material was commercially available was determined by silica gel column chromatography.

Malodorous materials were quantified using No. 77 series Detector Tube manufactured by GASTEC CORPORATION or NMR analysis.

Example 1

Deodorization Step of 3'-dimethylaminoacetophenone Solution Using Microreactor

The deodorization step was performed using the reactor shown in FIG. 1.

The 3'-dimethylaminoacetophenone solution (solution A) containing the malodorous material was prepared referring to the method described in J. Org. Chem., vol. 41, p. 957-962 (1976). In a methylene chloride solvent at −78° C., Swern oxidation reaction was performed using 10 mL of 1-(3-dimethylaminophenyl)ethanol (0.3 mol/L), 0.586 g of dimethyl sulfoxide, 1.575 g of trifluoroacetic anhydride, and 1.163 g of diisopropylethylamine, so that the desired ketone compound was obtained (reaction yield 85%) and then used. The oxidizing agent solution (solution B) used was so prepared that the amount of a sodium hypochlorite aqueous solution (concentration 13.3%) became 1.2 molar equivalent based on the amount of trifluoroacetic anhydride. The solutions A and B were each sucked into a glass syringe and then fed to the microreactor using Syringe Pump model PHD-2000 manufactured by Harvard Apparatus. The solution A was supplied at a flow rate of 1.5 mL/min to the microreactor, and the solution B was supplied at a flow rate of 1.5 mL/min. In this process, the diameter of the flow passage (the inner diameter of the micromixer) was 0.25 mm at sections 3 to 5 and 4 to 5, and immediately downstream of point 5 in the micromixer of FIG. 1. The retention time at sections 5 to 6 was 0.5 seconds. The reaction temperature was 30° C. After a waiting time of 3 minutes, the reaction liquid flowing out of the exit of the reactor was sampled for 15 seconds into a sampling tube containing 1 mL of pure water and then stirred at 25° C. for 10 seconds. The reaction solution was analyzed using HPLC, in which quantitative analysis was performed by internal standardization using a standard material. As a result, the yield of the desired ketone compound (the total yield from 1-(3-dimethylaminophenyl) ethanol) was 84%, and no influence of the oxidation reaction on the substrate was observed.

Examples 2 to 16

Examples 2 to 16 were performed under the same conditions as those in Example 1, except that the reaction temperature and the retention time were changed to those shown in Table 1 below.

Comparative Example 1

Deodorization Step of 3'-dimethylaminoacetophenone Solution in a Batch Method

Solutions A and B were used, which were prepared in the same method as in Example 1. Beforehand, 4.5 mL of the solution B was added to a 25 mL flask containing a magnetic stirrer bar. At a temperature of 30° C., the solution A was then added at a rate of 1.5 mL/min dropwise to the flask with stirring. After the dropwise addition was completed, the mixture was stirred for 1 minute. The reaction solution was analyzed using HPLC, in which quantitative analysis was performed by internal standardization using a standard material. As a result, the yield of the desired ketone compound (the total yield) was 20%, which means that the oxidation reaction was accompanied by a side reaction with the substrate, so that the yield was significantly lowered.

Comparative Example 2

Deodorization Step of 3'-dimethylaminoacetophenone Solution in a Batch Method

Solutions A and B were used, which were prepared in the same method as in Comparative Example 1. Beforehand, 4.5 mL of the solution A was added to a 25 mL flask containing a magnetic stirrer bar. At a temperature of 30° C., the solution B was then added at a rate of 1.5 mL/min dropwise to the flask with stirring. After the dropwise addition was completed, the mixture was stirred for 1 minute. The reaction solution was analyzed using HPLC, in which quantitative analysis was performed by internal standardization using a standard material. As a result, the yield of the desired ketone compound (the total yield) was 25%, which means that even when the dropwise addition conditions were changed, the oxidation reaction was accompanied by a side reaction with the substrate, so that the yield was significantly lowered.

Comparative Example 3

Deodorization Step of 3'-dimethylaminoacetophenone Solution in a Batch Method

Solutions A and B were used, which were prepared in the same method as in Comparative Example 1. The solutions A and B were simultaneously added at a rate of 1.5 mL/min dropwise to a 25 mL flask containing a magnetic stirrer bar, and stirred at a temperature of 30° C. After the dropwise addition was completed, the mixture was stirred for 1 minute. The reaction solution was analyzed using HPLC, in which quantitative analysis was performed by internal standardization using a standard material. As a result, the yield of the desired ketone compound (the total yield) was 29%, which means that even when the dropwise addition conditions were changed to the simultaneous mode, the oxidation reaction was accompanied by a side reaction with the substrate, so that the yield was significantly lowered.

These results are comprehensively shown in Table 1.

Note that "residual DMS" indicates the yield of the dimethyl sulfide residue (based on a theoretical value).

TABLE 1

Ex's 1 to 16, C Ex's 1 to 3

Alcohol compound Reactant / Carbonyl compound Product

| Ex/C Ex Nos. | Reaction temperature (° C.) | Reaction time (sec.) | Total yield (%) | Residual DMS (%) |
|---|---|---|---|---|
| Ex 1 | 30 | 0.5 | 84 | 0.5 |
| Ex 2 | 20 | 0.5 | 85 | 0.7 |
| Ex 3 | 10 | 0.5 | 85 | 0.9 |
| Ex 4 | 0 | 0.5 | 84 | 0.9 |
| Ex 5 | 40 | 0.5 | 82 | 0.4 |
| Ex 6 | 50 | 0.5 | 79 | 0.3 |
| Ex 7 | 55 | 0.5 | 76 | 0.2 |
| Ex 8 | 60 | 0.5 | 73 | 0.2 |
| Ex 9 | 30 | 0.01 | 85 | 3.0 |
| Ex 10 | 30 | 1.0 | 83 | 0.2 |
| Ex 11 | 30 | 3.0 | 83 | 0.1 |
| Ex 12 | 30 | 5.0 | 83 | 0.1 |
| Ex 13 | 30 | 30 | 83 | 0.1 |
| Ex 14 | 30 | 60 | 81 | 0.1 |
| Ex 15 | 30 | 90 | 74 | 6.5 |
| Ex 16 | 30 | 120 | 65 | 9.8 |
| C Ex 1 | 30 | 60 | 20 | 53 |
| C Ex 2 | 30 | 60 | 25 | 51 |
| C Ex 3 | 30 | 60 | 29 | 48 |

'Ex' means Example according to this invention, and 'C Ex' means Comparative Example.

Examples 17 to 21

Examples 17 to 21 were performed under the same conditions as those in Example 1, except that the oxidizing agent was changed to that shown in Table 2 below.

Examples 18 to 21 were performed using methylene chloride solutions.

These results are comprehensively shown in Table 2.

TABLE 2

| Ex's Nos. | Kind of oxidizing agent | Total yield (%) | Residual DMS (%) |
|---|---|---|---|
| Ex 17 | Peracetic acid/hydrogen peroxide solution | 79 | 0.1 |
| Ex 18 | N-Chlorosuccinimide | 85 | 0.1 |
| Ex 19 | N-Bromosuccinimide | 84 | 0.1 |
| Ex 20 | 1,3-Dichloro-5,5-dimethylhydantoin | 83 | 0.1 |
| Ex 21 | 1,3-Dibromo-5,5-dimethylhydantoin | 82 | 0.1 |

'Ex' means Example according to this invention.

Examples 22 to 26

Examples 22 to 26 were performed under the same conditions as those in Example 1, except that the oxidizing agent solution of Example 18 was used under the modified conditions shown in Table 3 below.

These results are comprehensively shown in Table 3.

TABLE 3

| Ex's Nos. | Reaction temperature (° C.) | Total yield (%) | Residual DMS (%) |
|---|---|---|---|
| Ex 22 | −20 | 85 | 5.0 |
| Ex 23 | −10 | 85 | 2.9 |
| Ex 24 | −5 | 85 | 1.8 |
| Ex 25 | 0 | 85 | 0.8 |
| Ex 26 | 40 | 82 | 0.1 |

'Ex' means Example according to this invention.

Examples 27 to 33

Examples 27 to 33 were performed under the same conditions as those in Example 1, except that the amount of the oxidizing agent was changed to the equivalent amount (molar equivalent amount) shown in Table 4 below.

These results are comprehensively shown in Table 4.

TABLE 4

| Ex's Nos. | Equivalent amount of oxidizing agent | Total yield (%) | Residual DMS (%) |
|---|---|---|---|
| Ex 27 | 0.5 | 85 | 33.4 |
| Ex 28 | 0.8 | 85 | 10.3 |
| Ex 29 | 1.0 | 85 | 0.7 |
| Ex 30 | 2.0 | 82 | 0.2 |
| Ex 31 | 3.0 | 82 | 0.2 |
| Ex 32 | 4.0 | 82 | 0.2 |
| Ex 33 | 5.0 | 81 | 0.1 |

'Ex' means Example according to this invention.

Examples 34 to 38

Examples 34 to 38 were performed under the same conditions as those in Example 1, except that the inner diameter (flow passage diameter) of the micromixer of FIG. 1 was changed to that shown in Table 5 below.

These results are comprehensively shown in Table 5.

TABLE 5

| Ex's Nos. | Flow passage diameter (mm) | Total yield (%) | Residual DMS (%) |
|---|---|---|---|
| Ex 34 | 0.15 | 85 | 0.1 |
| Ex 35 | 0.5 | 84 | 0.1 |
| Ex 36 | 0.8 | 84 | 0.2 |
| Ex 37 | 1.0 | 82 | 0.5 |
| Ex 38 | 1.5 | 80 | 0.9 |

'Ex' means Example according to this invention.

Examples 39 to 47

Examples 39 to 47 were performed under the same conditions as those in Example 1, except that the alcohol compound (reactant) was changed to that shown in Table 6 below.

These results are comprehensively shown in Table 6.

Note that the yield of the carbonyl compound (product) was the yield in the Swern oxidation reaction with the solution A.

TABLE 6

| Ex's Nos. | Alcohol compound Reactant | Carbonyl compound Product | Yield (%) of carbonyl compound | Total yield (%) | Residual DMS (%) |
|---|---|---|---|---|---|
| Ex 39 | diphenylmethanol | benzophenone | 92 | 91 | 0.3 |
| Ex 40 | 1-(4-bromophenyl)ethanol | 1-(4-bromophenyl)ethanone | 95 | 94 | 0.4 |
| Ex 41 | cinnamyl alcohol | cinnamaldehyde | 93 | 92 | 0.1 |
| Ex 42 | 1-decanol | decanal | 72 | 71 | 0.2 |
| Ex 43 | 2-octanol | 2-octanone | 81 | 80 | 0.1 |
| Ex 44 | cyclohexanol | cyclohexanone | 88 | 87 | 0.2 |
| Ex 45 | furfuryl alcohol | furfural | 91 | 90 | 0.7 |

TABLE 6-continued

| Ex's Nos. | Alcohol compound Reactant | Carbonyl compound Product | Yield (%) of carbonyl compound | Total yield (%) | Residual DMS (%) |
|---|---|---|---|---|---|
| Ex 46 | [structure] | [structure] | 75 | 74 | 0.8 |
| Ex 47 | [structure] | [structure] | 73 | 72 | 0.3 |

'Ex' means Example according to this invention.

Example 48

Deodorization Step of 3'-dimethylaminoacetophenone Solution Using Microreactor (Using Corey-Kim Oxidation Reaction Solution)

The deodorization step was performed using the reactor shown in FIG. 1.

The 3'-dimethylaminoacetophenone solution (solution A) containing the malodorous material was prepared referring to the method described in J. Am. Chem. Soc., vol. 94, p. 7586-7587 (1972).

In a methylene chloride solvent at −20° C., Corey-Kim oxidation reaction was performed using 10 mL of 1-(3-dimethylaminophenyl)ethanol (0.3 mol/L), 0.391 g of dimethyl sulfide, 0.601 g of N-chlorosuccinimide, and 0.455 g of triethylamine, so that the desired ketone compound was obtained (reaction yield 89%) and then used. The oxidizing agent solution (solution B) used was so prepared that the amount of a sodium hypochlorite aqueous solution (concentration 13.3%) became 2.0 molar equivalent based on the amount of N-chlorosuccinimide. The solutions A and B were each sucked into a glass syringe and then fed to the microreactor using Syringe Pump model PHD-2000 manufactured by Harvard Apparatus. The solution A was supplied at a flow rate of 1.5 mL/min to the microreactor, and the solution B was supplied at a flow rate of 1.5 mL/min. In this process, the diameter of the flow passage (the inner diameter of the micromixer) was 0.25 mm at sections 3 to 5 and 4 to 5, and immediately downstream of point 5 in the micromixer of FIG. 1. The retention time at sections 5 to 6 was 0.5 seconds. The reaction temperature was 30° C. After a waiting time of 3 minutes, the reaction liquid flowing out of the exit of the reactor was sampled for 15 seconds into a sampling tube containing 1 mL of pure water and then stirred at 25° C. for 10 seconds. The reaction solution was analyzed using HPLC, in which quantitative analysis was performed by internal standardization using a standard material. As a result, the yield of the desired ketone compound (the total yield) was 88%, and no influence of the oxidation reaction on the substrate was observed.

Examples 49 to 51

Examples 49 to 51 were performed under the same conditions as those in Example 48, except that the kind of alcohol compound (reactant) was changed to that shown in Table 7 below.

These results including that of Example 48 are comprehensively shown in 7.

Note that "residual DMS" indicates the yield of the dimethyl sulfide residue (based on a theoretical value).

TABLE 7

| Ex's Nos. | Alcohol compound Reactant | Carbonyl compound Product | Yield (%) of carbonyl compound | Total yield (%) | Residual DMS (%) |
|---|---|---|---|---|---|
| Ex 48 | 3-(dimethylamino)-α-methylbenzyl alcohol | 3'-(dimethylamino)acetophenone | 89 | 88 | 0.9 |
| Ex 49 | 4-(dimethylamino)benzyl alcohol | 4-(dimethylamino)benzaldehyde | 80 | 78 | 1.5 |
| Ex 50 | 1-(pyridin-2-yl)ethanol | 2-acetylpyridine | 75 | 73 | 2.3 |
| Ex 51 | testosterone | androstenedione | 94 | 93 | 0.3 |

'Ex' means Example according to this invention.

Example 52

Integrated Reaction Process of Swern Oxidation Reaction and Deodorization Step Using Microreactor The reaction step and the deodorization step were performed using the reactor shown in FIG. 2.

The solutions used were a methylene chloride solution of a mixture of 1-(3-dimethylaminophenyl)ethanol (0.06 M) and dimethyl sulfoxide (0.15 M) with the adjusted concentrations (solution A1), a trifluoroacetic anhydride/methylene chloride solution (0.15 M) (solution A2), a diisopropylethylamine/methylene chloride solution (0.18 M) (solution A3), and a solution (0.18 M) prepared in such a method that the amount of a sodium hypochlorite aqueous solution (concentration 13.3%) became 1.2 molar equivalent based on the amount of trifluoroacetic anhydride (solution B).

Pump LC-20AT or LC-10Ai manufactured by SHIMADZU CORPORATION was used to feed the solutions A1, A2, A3, and B to the microreactor. The solutions A1 to A3 and B were supplied at a flow rate of 1.5 mL/min to the microreactor. In this process, the retention time at sections 12 to 14, 15 to 17, and 18 to 20 in the micromixer of FIG. 2 were 0.05 seconds, 6.9 seconds, and 0.5 seconds, respectively. The diameter of the flow passage (the inner diameter of the micromixer) was 0.25 mm at sections 11 to 12, 13 to 12, 14 to 15, 16 to 15, 17 to 18, and 19 to 18, and immediately downstream of points 12, 15, and 18. The reaction temperature was 0° C. at sections 7 to 14 and 8 to 14, and 30° C. at sections 14 to 20, 9 to 20, and 10 to 20. After a waiting time of 3 minutes, the reaction liquid flowing out of the exit of the reactor was sampled for 15 seconds into a sampling tube containing 1 mL of pure water and then stirred at 25° C. for 10 seconds. The reaction solution was analyzed using HPLC, in which quantitative analysis was performed by internal standardization using a standard material. As a result, the total yield of the desired ketone compound (yield after the deodorization step) was 90%, and no influence of the oxidation reaction on the substrate was observed.

Examples 53 to 55

Examples 53 to 55 were performed under the same conditions as those in Example 52, except that the kind of reactant was changed to that shown in Table 8 below.

These results including that of Example 52 are comprehensively shown in Table 8.

Note that "residual DMS" indicates the yield of the dimethyl sulfide residue (based on a theoretical value).

Moreover, "Bz" represents a benzoyl group (—C(=O)—$C_6H_5$).

TABLE 8

| Ex's Nos. | Alcohol compound Reactant | Carbonyl compound Product | Total yield (%) | Residual DMS (%) |
|---|---|---|---|---|
| Ex 52 | [structure: 1-(3-dimethylaminophenyl)ethanol] | [structure: 1-(3-dimethylaminophenyl)ethanone] | 90 | 0.3 |
| Ex 53 | [structure: diphenylmethanol] | [structure: benzophenone] | 94 | 0.1 |
| Ex 54 | [macrolide structure with HO groups] | [macrolide structure with ketone] | 87 | 0.4 |
| Ex 55 | [azido macrolide structure with OH] | [azido macrolide structure with ketone] | 94 | 0.2 |

'Ex' means Example according to this invention.

Examples 56 to 60

Examples 56 to 60 were performed under the same conditions as those in Example 52, except that the compound for use in Example 55 was used as the reactant and the oxidizing agent was changed to that shown in Table 9 below.

Examples 57 to 60 were performed using methylene chloride solutions.

These results are comprehensively shown in Table 9.

TABLE 9

| Ex's Nos. | Kind of oxidizing agent | Total yield (%) | Residual DMS (%) |
|---|---|---|---|
| Ex 56 | Peracetic acid/hydrogen peroxide solution | 89 | 0.1 |
| Ex 57 | N-Chlorosuccinimide | 94 | 0.1 |
| Ex 58 | N-Bromosuccinimide | 93 | 0.1 |
| Ex 59 | 1,3-Dichloro-5,5-dimethylhydantoin | 92 | 0.1 |
| Ex 60 | 1,3-Dibromo-5,5-dimethylhydantoin | 92 | 0.1 |

'Ex' means Example according to this invention.

Example 61

Integrated Reaction Process of Corey-Kim Oxidation Reaction and Deodorization Step Using Microreactor The reaction step and the deodorization step were performed using the reactor shown in FIG. 2.

The solutions used were a methylene chloride solution of a mixture of 1-(3-dimethylaminophenyl)ethanol (0.06 M) and dimethyl sulfide (0.13 M) with the adjusted concentrations (solution A1), a N-chlorosuccinimide/methylene chloride solution (0.09 M) (solution A2), a triethyl amine/methylene chloride solution (0.09 M) (solution A3), and a solution (0.18 M) prepared in such a method that the amount of a sodium hypochlorite aqueous solution (concentration 13.3%) became 2.0 molar equivalent based on the amount of N-chlorosuccinimide (solution B).

Pump LC-20AT or LC-10Ai manufactured by SHIMADZU CORPORATION was used to feed the solutions A1, A2, A3, and B to the microreactor. The solutions A1 to A3 and B were supplied at a flow rate of 1.5 mL/min to the microreactor. In this process, the retention time at sections 12 to 14, 15 to 17, and 18 to 20 in the micromixer of FIG. 2 were 10.5 seconds, 15.8 seconds, and 0.5 seconds, respectively. The diameter of the flow passage (the inner diameter of the micromixer) was 0.25 mm at sections 11 to 12, 13 to 12, 14 to 15, 16 to 15, 17 to 18, and 19 to 18, and immediately downstream of points 12, 15, and 18. The reaction temperature was −10° C. at sections 7 to 14 and 8 to 14, and 30° C. at sections 14 to 20, 9 to 20, and 10 to 20.

After a waiting time of 3 minutes, the reaction liquid flowing out of the exit of the reactor was sampled for 15 seconds into a sampling tube containing 1 mL of pure water and then stirred at 25° C. for 10 seconds. The reaction solution was analyzed using HPLC, in which quantitative analysis was performed by internal standardization using a standard material. As a result, the total yield of the desired ketone compound (yield after the deodorization step) was 90%, and no influence of the oxidation reaction on the substrate was observed.

Examples 62 to 66

Examples 62 to 66 were performed under the same conditions as those in Example 61, except that the reactant was changed to that shown in Table 10 below.

These results including that of Example 61 are comprehensively shown in Table 10.

Note that "residual DMS" indicates the yield of the dimethyl sulfide residue (based on a theoretical value)

TABLE 10

| Ex's Nos. | Alcohol compound Reactant | Carbonyl compound Product | Total yield (%) | Residual DMS (%) |
|---|---|---|---|---|
| Ex 61 | (structure) | (structure) | 90 | 0.3 |
| Ex 62 | (structure) | (structure) | 81 | 1.4 |
| Ex 63 | (structure) | (structure) | 75 | 2.1 |
| Ex 64 | (structure) | (structure) | 70 | 0.6 |

TABLE 10-continued

| Ex's Nos. | Alcohol compound Reactant | Carbonyl compound Product | Total yield (%) | Residual DMS (%) |
|---|---|---|---|---|
| Ex 65 | [structure] | [structure] | 92 | 0.8 |
| Ex 66 | [structure] | [structure] | 91 | 0.3 |

'Ex' means Example according to this invention.

Tables 1 to 10 described above show that when the deodorization step for removing, from a reaction liquid, a malodorous material generated or remaining in the reaction step was performed using a flow reaction in a flow passage, efficient deodorization treatment of merely the malodorous material was possible with no influence on the aldehyde or ketone compound produced in the reaction step.

Having described our invention as related to the present embodiments, it is our intention that the invention not be limited by any of the details of the description, unless otherwise specified, but rather be construed broadly within its spirit and scope as set out in the accompanying claims.

This application claims priority on Patent Application No. 2015-195375 filed in Japan on Sep. 30, 2015, which is entirely herein incorporated by reference.

REFERENCE SIGNS LIST

1, 2 Port for supplying a raw material to the microreactor
3, 4 Port for supplying a raw material to the micromixer
5 Start point of mixing of the solutions A and B
6 Exit of the microreactor
7, 8, 9, 10 Port for supplying a raw material to the microreactor
11, 13, 14, 16, 17, 19 Port for supplying a raw material to the micromixer
12 Mixing start point in a first step (a reaction between solutions A1 and A2)
15 Mixing start point in a second step (a reaction with solution A3)
18 Mixing start point in a third step (a reaction with solution B)
20 Exit of the microreactor

The invention claimed is:

1. A method of producing an organic compound, comprising:
    performing a deodorization using a flow reaction in a flow passage to remove, from a reaction liquid, a malodorous material generated or remaining in a reaction,
    wherein the organic compound is an industrially useful compound.

2. The production method according to claim 1, wherein the reaction is an oxidation reaction using a sulfur atom-containing organic compound.

3. The production method according to claim 1, wherein, in the reaction, an alcohol compound having 2 to 50 carbon atoms is oxidized to produce an aldehyde or ketone compound having 2 to 50 carbon atoms.

4. The production method according to claim 2, wherein the oxidation reaction using a sulfur-atom-containing organic compound is an oxidation reaction using a dialkyl sulfoxide compound having 2 to 8 carbon atoms, and an acid anhydride having 4 to 10 carbon atoms or an acid halide having 2 to 7 carbon atoms.

5. The production method according to claim 1, wherein the malodorous material is a dialkyl sulfide having 2 to 8 carbon atoms.

6. The production method according to claim 1, wherein the deodorization is an oxidation reaction of the malodorous material.

7. The production method according to claim 1, wherein the deodorization is an oxidation reaction in which the malodorous material is oxidized by using an oxidizing agent selected from the group consisting of hypochlorous acid or a salt thereof, a halogenating agent, and peracetic acid.

8. The production method according to claim 7, wherein an amount of the oxidizing agent is 0.5 to 5.0 molar equivalents, based on an amount of the acid anhydride or the acid halide in the reaction.

9. The production method according to claim 1, wherein a reaction temperature in the deodorization is in a range of from −20° C. to 60° C.

10. The production method according to claim 1, wherein a time for which the deodorization is retained in the flow passage is in a range of from 0.01 to 120 seconds.

11. The production method according to claim 3, wherein the alcohol compound is a compound of Formula (A), and the organic compound is a compound of Formula (B):

Formula (A)

Formula (B)

where $R^3$ represents a hydrogen atom, an alkyl group, a cycloalkyl group, an alkenyl group, a cycloalkenyl group, an aryl group, or a heterocyclic group; $R^4$ represents an alkyl group, a cycloalkyl group, an alkenyl group, a cycloalkenyl group, an aryl group, or a heterocyclic group; and $R^3$ and $R^4$ may combine together to form a ring.

12. The production method according to claim 1, wherein the reaction and the deodorization are both flow reactions in the flow passage and performed sequentially.

13. The production method according to claim 1, wherein the deodorization is conducted in a microreactor.

14. The production method according to claim 2, wherein, in the reaction, an alcohol compound having 2 to 50 carbon atoms is oxidized to produce an aldehyde or ketone compound having 2 to 50 carbon atoms.

15. The production method according to claim 3, wherein the oxidation reaction using a sulfur-atom-containing organic compound is an oxidation reaction using a dialkyl sulfoxide compound having 2 to 8 carbon atoms, and an acid anhydride having 4 to 10 carbon atoms or an acid halide having 2 to 7 carbon atoms.

16. The production method according to claim 2, wherein the malodorous material is a dialkyl sulfide having 2 to 8 carbon atoms.

17. The production method according to claim 2, wherein the deodorization is an oxidation reaction of the malodorous material.

18. The production method according to claim 2, wherein the deodorization is an oxidation reaction in which the malodorous material is oxidized by using an oxidizing agent selected from the group consisting of hypochlorous acid or a salt thereof, a halogenating agent, and peracetic acid.

19. The production method according to claim 18, wherein an amount of the oxidizing agent is 0.5 to 5.0 molar equivalents, based on an amount of the acid anhydride or the acid halide in the reaction.

20. The production method according to claim 2, wherein a reaction temperature in the deodorization is in a range of from −20° C. to 60° C.

21. A method of producing an organic compound, comprising:
    mixing a solution including a raw material and a solution including an activator such that the raw material and the activator undergo an oxidation reaction and that a reaction liquid including an organic compound and a malodorous material is obtained; and
    passing the reaction liquid through a flow passage such that the reaction liquid undergoes a flow reaction in the flow passage to remove, from the reaction liquid, the malodorous material.

* * * * *